United States Patent
Abbott et al.

(10) Patent No.: US 11,967,871 B2
(45) Date of Patent: Apr. 23, 2024

(54) COGGING-TORQUE ACTUATOR

(71) Applicant: University of Utah Research Foundation, Salt Lake City, UT (US)

(72) Inventors: Jacob J Abbott, Salt Lake City, UT (US); Shad Roundy, Salt Lake City, UT (US); Jacob Aman, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 600 days.

(21) Appl. No.: 16/647,816

(22) PCT Filed: Sep. 17, 2018

(86) PCT No.: PCT/US2018/051376
§ 371 (c)(1),
(2) Date: Mar. 16, 2020

(87) PCT Pub. No.: WO2019/055937
PCT Pub. Date: Mar. 21, 2019

(65) Prior Publication Data
US 2020/0274431 A1    Aug. 27, 2020

Related U.S. Application Data

(60) Provisional application No. 62/559,381, filed on Sep. 15, 2017.

(51) Int. Cl.
*H02K 21/20* (2006.01)
*A61F 2/70* (2006.01)
(Continued)

(52) U.S. Cl.
CPC ............... *H02K 21/20* (2013.01); *A61F 2/70* (2013.01); *A61H 3/00* (2013.01); *H02K 3/20* (2013.01);
(Continued)

(58) Field of Classification Search
CPC ........ H02K 21/20; H02K 11/21; H02K 11/24; H02K 3/20; A61F 2/70; A61F 2002/6863;
(Continued)

(56) References Cited

U.S. PATENT DOCUMENTS

| 4,137,489 A | 1/1979 | Lipo |
| 4,501,980 A | 2/1985 | Welburn |

(Continued)

FOREIGN PATENT DOCUMENTS

JP    2011256544 A    12/2011

OTHER PUBLICATIONS

Bianchi et al.; "Design techniques for reducing the cogging torque in surface-mounted PM motors." IEEE Transactions on Industry Applications; IEEE; Nov. 7, 2002; vol. 38, Issue 5; pp. 1259-1265.

(Continued)

*Primary Examiner* — Matthew J Lawson
*Assistant Examiner* — Aren Patel
(74) *Attorney, Agent, or Firm* — Thorpe North & Western, LLP.

(57) ABSTRACT

An electromagnetic actuator for non-continuous rotation (cogging-torque actuator (CTA)) (100) comprises a support structure (116), an output shaft (104) rotatable about and defining an axis of rotation (X), a permanent magnet rotor (106) comprising at least two magnetic poles (108a, 108b) attached to the output shaft (104), and a stator device (110) comprising a ferromagnetic pole body (112) attached to the support structure (116) and surrounding the at least two magnetic poles (108a, 108b). The ferromagnetic pole body (112) can have at least four ferromagnetic stator poles (112a-d) each wrapped in a conductive wire (114a-d) to define a stator coil. The at least four ferromagnetic stator poles (112a-d) are sized, and spaced radially from each other, so as to define a maximum cogging torque of the (Continued)

electromagnetic actuator (100). The CTA (100) can operate as an actuator, an elastic spring, a clutch, and/or a load support device.

21 Claims, 13 Drawing Sheets

(51) Int. Cl.
| | |
|---|---|
| *A61H 3/00* | (2006.01) |
| *H02K 3/20* | (2006.01) |
| *H02K 11/21* | (2016.01) |
| *H02K 11/24* | (2016.01) |
| *A61F 2/68* | (2006.01) |
| *A61F 2/76* | (2006.01) |

(52) U.S. Cl.
CPC ............. *H02K 11/21* (2016.01); *H02K 11/24* (2016.01); *A61F 2002/6863* (2013.01); *A61F 2002/704* (2013.01); *A61F 2002/7635* (2013.01); *A61H 2201/1215* (2013.01); *A61H 2201/1659* (2013.01); *A61H 2201/5061* (2013.01)

(58) Field of Classification Search
CPC ....... A61F 2002/704; A61F 2002/7635; A61H 3/00; A61H 2201/1215; A61H 2201/1659; A61H 2201/5061
See application file for complete search history.

(56) References Cited

U.S. PATENT DOCUMENTS

| | | | |
|---|---|---|---|
| 4,520,300 A | 5/1985 | Fradella | |
| 4,661,756 A | 4/1987 | Murphy et al. | |
| 4,774,425 A | 9/1988 | Rusu et al. | |
| 5,059,884 A | 10/1991 | Shah et al. | |
| 5,523,637 A | 6/1996 | Miller | |
| 5,677,581 A | 10/1997 | Yoshida et al. | |
| 5,679,997 A | 10/1997 | Matsuzawa et al. | |
| 5,757,100 A | 5/1998 | Bu | |
| 5,990,592 A | 11/1999 | Miura et al. | |
| 6,081,058 A | 6/2000 | Suzuki et al. | |
| 6,940,198 B2 | 9/2005 | Ionel et al. | |
| 7,148,592 B2 | 12/2006 | Miyawaki | |
| 7,538,469 B2 | 5/2009 | Thornton et al. | |
| 7,588,002 B2 | 9/2009 | Wygnanski et al. | |
| 7,898,135 B2 | 3/2011 | Flynn | |
| 8,598,757 B2 | 12/2013 | Hsu et al. | |
| 8,816,554 B2 | 8/2014 | Li et al. | |
| 8,975,854 B1 | 3/2015 | Poulad et al. | |
| 9,356,500 B2 | 5/2016 | Furlan et al. | |
| 2003/0098660 A1 | 5/2003 | Erdman et al. | |
| 2004/0021437 A1 | 2/2004 | Maslov et al. | |
| 2004/0075407 A1 | 4/2004 | Ohiwa et al. | |
| 2005/0269892 A1 | 12/2005 | Duff, Jr. | |
| 2008/0278015 A1 | 11/2008 | Reisinger | |
| 2011/0125290 A1* | 5/2011 | Langlois | A61F 2/60 623/27 |
| 2011/0181135 A1* | 7/2011 | Pollock | H02P 8/22 310/49.46 |
| 2012/0032545 A1* | 2/2012 | Hsu | H02K 29/03 310/114 |
| 2012/0080968 A1 | 4/2012 | Knight et al. | |
| 2013/0278086 A1 | 10/2013 | Furlan et al. | |
| 2015/0127118 A1 | 5/2015 | Herr et al. | |
| 2015/0139770 A1* | 5/2015 | Moura | H02K 1/24 310/68 B |
| 2017/0198728 A1* | 7/2017 | Noda | F15B 15/125 |
| 2017/0257043 A1* | 9/2017 | Lorilla | H02P 6/10 |
| 2017/0264178 A1* | 9/2017 | Stauder | H02K 11/33 |
| 2019/0199147 A1* | 6/2019 | Woo | H02K 21/16 |

OTHER PUBLICATIONS

PCT Application No. PCT/US18/51376 Filing date Sep. 17, 2018, Jacob J. Abbot International Search Report dated Jan. 16, 2019; 11 Pages.

Zhu et al.; "Influence of design parameters on cogging torque in permanent magnet machines." IEEE Transactions on Energy Conversion; IEEE; Dec. 2000; vol. 15, Issue 4; pp. 407-412.

Reinholz; "A Cogging-Torque-Assisted Motor Drive for Internal Combustion Engine Valbves;" Master of Applied Science, The University of British Columbia; (2014); 97 pages.

Sudano et al.; "A Resonant Parallel Elastic Actuator for Biorobotic Applications;" Università Campus Bio-Medico di Roma, Laboratory of Biomedical Robotics and Biomicrosystems, Center of Integrated Research (CIR); Conference Paper; (Sep. 2014); 7 pages; <doi:10.1109/IROS.2014.6942948>.

* cited by examiner

COGGING-TORQUE ACTUATOR

RELATED APPLICATION(S)

This application claims priority to U.S. Provisional Application No. 62/559,381, filed Sep. 15, 2017 which is incorporated herein by reference.

BACKGROUND

Most robots are actuated by continuous rotational electromagnetic machines (i.e., motors). Motors were designed for industrial processes in which continuous smooth rotation is desirable. They are the primary choice for robotic actuators due to their technological maturity, their ability to run off of electricity (e.g., batteries), and the fact that they are clean and quiet. However, they have a number of shortcomings for use in agile robots. Some of their deficiencies include that: (1) motors are designed to rotate efficiently at high speeds and must typically be geared down to achieve velocities typical of robot applications; (2) direct-drive motors are easy to model and control as torque sources, but they are weak for their size; (3) in order to hold a position under load, direct-drive and lightly geared motors must either continuously supply electrical power to the motor or use a brake mechanism; and (4) heavily geared motors are inefficient, and are designed with no inherent compliance or backdrivability. Compliance in actuators is important for human safety and to prevent damage to the robot, and has been shown to improve control robustness in many robotics applications; compliance is also biology's solution to robust mobility and manipulation.

There is an inherent tradeoff between the ability for a robotic actuator to be backdriven and the ability to passively hold a static position under load, otherwise known as a "holding torque". Holding torque can be achieved by incorporating a brake mechanism with the electromagnetic motor/actuator. However, brakes mechanisms typically cannot be backdriven without substantial complexity of additional components and control schemes.

Compliance has been added to robotic actuators as series-elastic actuators, antagonistic elastic actuators, etc. Series-clutch actuators have been proposed that use a brake to hold position. However, to address these issues with auxiliary add-ons to motors or hydraulic actuators results in large and complex actuation systems. Furthermore, with such complex systems it is very difficult to implement distributed control and to take advantage of the nonlinear passive dynamics of the actuators.

Brushless permanent-magnet DC motors are a popular choice for robotic applications. The typical geometric variables available to designers include gap radius, rotor length, and rotor pole and stator pole configurations. These geometries are varied to maximize some performance outcome; however, a fundamental re-design of the motor architecture has not been undertaken for robotics. Designers of brushless permanent magnet motors have traditionally had to deal with addressing and minimizing cogging torque. Cogging torque is the rate change of the magnetic energy with the angular position with null rotor currents. Cogging torque is caused by the interaction of rotor magnets with stator slots (i.e., the space between stator poles). The cogging torque causes variations in motor output torque, and is a key contributor to "torque ripple." In motor design, these deviations of torque for a given input are unwanted and considered a parasitic element, and have been studied extensively for decades, with researchers trying to mechanically and electrically eliminate such cogging torque. Common methods of minimizing cogging torque include stator pole shoe design, stator notches, and skewing.

Humans are able to operate quickly and effectively in very complex and dynamic environments despite the fact that the human neuromuscular system is comparatively very slow. The fastest neural transmission speed for humans is about 120 m/s and the typical muscular twitch contraction time is on the order of 50 ms. Assuming a linearized model, this implies a bandwidth of about 3 Hz, which is much slower than standard electromechanical technology. Nevertheless, humans routinely perform actions with much better dexterity and speed than machines. There is a growing body of evidence that one of the enabling factors of human dexterity is the fact that sensorimotor control relies on the composition of primitive dynamic actions. The evidence suggests that humans control motion by a combination of small, relatively fast, pre-learned motion primitives. Each motion primitive can be thought of as an open-loop event from the perspective of the brain. The brain then commands control in more of a supervisory fashion, stringing together these motion primitives. Some researchers have proposed three fundamental motion primitives used by humans: mechanical impedances, point-to-point sub-movements, and oscillations.

SUMMARY

The present disclosure sets forth an electromagnetic actuator for non-continuous rotation (referred to herein as a cogging-torque actuator (CTA)) comprising a support structure with an output shaft rotatable about and defining an axis of rotation. A permanent magnet rotor can comprise at least two magnetic poles attached to the output shaft. A corresponding stator device can comprise a ferromagnetic pole body attached to the support structure and surrounding the at least two magnetic poles. The ferromagnetic pole body can have at least four ferromagnetic stator poles each wrapped in a conductive wire to define a stator coil. These ferromagnetic stator poles are sized, and spaced radially from each other, so as to define a maximum cogging torque of the electromagnetic actuator. Furthermore, a total torque of the electromagnetic actuator (i.e. maximum cogging torque plus electromagnetic torque) can be within a same order of magnitude as the maximum cogging torque.

The electromagnetic actuator, or CTA, can optionally further comprise a controller operably coupled to the stator coils for controlling an electrical field applied to opposing stator coils. The controller can be operable to implement one or more motion primitives associated with rotational movement of the output shaft. The one or more motion primitives can comprise control over mechanical impedance, such that the controller is operable to modify a magnetic spring or damping value of the electromagnetic actuator by supplying an electrical field to opposing stator coils.

In one particular optional example, the one or more motion primitives comprise control over point-to-point sub-movements of the permanent magnet rotor in a rotational step movement relative to the stator device. The controller operates to apply an electrical field to opposing stator coils to rotate the permanent magnet rotor from a first step position to a second step position based on a sensed torque load on the output shaft. When in the second step position, the controller operates to remove the electrical field, such that one of the stator poles magnetically maintains the position of the permanent magnet rotor in the second step position in the absence of an applied electric field.

In another optional example, the controller is operable to cause rotation of the output shaft and the permanent magnet rotor in a plurality of consecutive step positions over a given period of time by controlling application of an electrical field to and from opposing stator coils.

In another optional example, the total torque comprises a combination of the maximum cogging torque and an applied electromagnetic torque, and the applied electromagnetic torque is greater than the maximum cogging torque, such that in addition to a torque load applied to the output shaft the applied electromagnetic torque is sufficient to overcome the maximum cogging torque to move the permanent magnet rotor from one step position to an adjacent step position relative to the stator device. Furthermore, as a general guideline a minimum total torque can be greater than the maximum cogging torque in order to avoid orientations which result in an immovable position without additional external applied torque.

In yet another optional example, the electromagnetic actuator serves as a torque sensor associated with the output shaft to determine a torque load applied to the output shaft.

The present disclosure also sets forth a system for controlling rotational movement of a joint comprising first and second support members rotatably coupled to each other and that define a joint rotatable about an axis of rotation. The system comprises an electromagnetic joint module comprising an input member coupled to the first support member, and an output shaft coupled to the second support member. The input member and the output shaft are rotatable about the axis of rotation. The electromagnetic joint module can comprise a CTA. For example, at least two magnetic poles can be attached to the output shaft, and a ferromagnetic stator pole body can be attached to the input member. A plurality of ferromagnetic stator poles can each be wrapped in a conductive wire to define a stator pole. The at least two magnetic poles and the plurality of ferromagnetic stator poles are also configured to define a maximum cogging torque. A controller can be operably coupled to each stator coil for controlling non-continuous rotational movement of the joint.

The present disclosure further sets forth a complementary method of operating the electromagnetic actuator. The method can comprise applying a torque load to an output shaft and applying an electrical field to opposing stator coils to rotate the output shaft from a first position to a second position sufficient to overcome the torque load. The method can further comprise removing the electrical field from the opposing stator coils, such that the output shaft remains in the second position to support the torque load by virtue of a magnetic force and magnetic torque generated by the permanent magnet rotor and the ferromagnetic pole body.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1A:
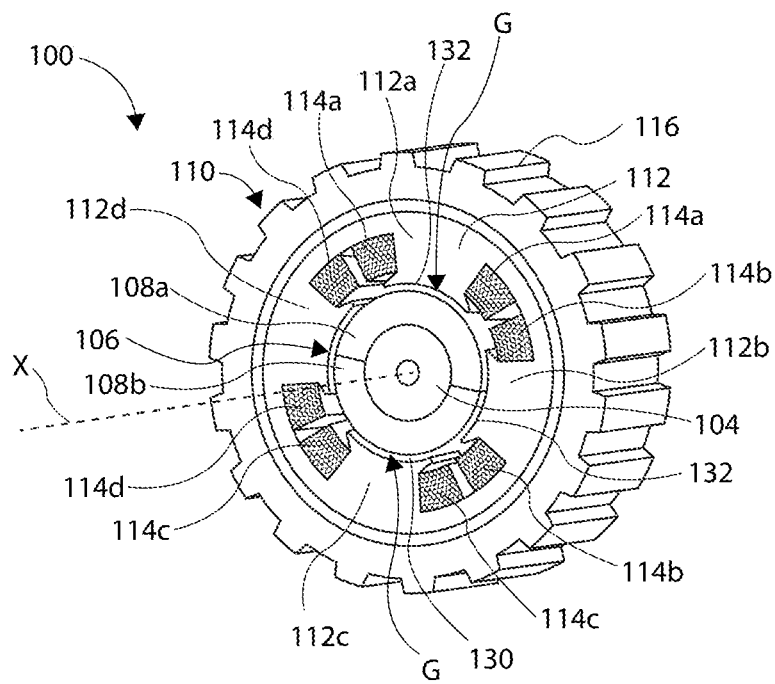
FIG. 1A is an isometric view of a cross section of a Cogging Torque Actuator (CTA) in accordance with an example of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a rotor" includes reference to one or more of such materials and reference to "aligning" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, "non-continuous rotation" refers to a rotation in which the desired angular position of the output shaft is specified using a sequence of discrete steps, as opposed to specifying a desired angular velocity of the output shaft.

As used herein, "maximum" refers to a global or local peak value obtained for a given variable based on input parameters. However, when referring to "a maximum cogging torque" such a value is fixed for a given CTA configuration. Thus, each CTA design will have "a maximum cogging torque" even though a higher cogging torque could be achieved by variation of the design (e.g. varied number of stator poles, increased gaps, etc). Thus, a maximum can be optimized by varying design parameters as discussed herein. Functional CTA configurations are thus not dependent on having "a maximum cogging torque" alone, but rather such a parameter which is also within a same order of magnitude as the total torque.

As used herein, "minimum" refers to a global or local low value obtained for a given variable based on input parameters. However, when referring to "a minimum total torque" such a value is fixed for a given CTA configuration and current density applied to the stator coils. Thus, each CTA design will have "a minimum total torque" for a given stator current density even though a lower total torque could be achieved by variation of the design (e.g. varied number of stator poles, increased gaps, etc) or a reduction in current density.

As used herein, and known in the industry, one order of magnitude can be defined as relative quantities or values being within 10 times of each other. And, two orders of magnitude would be within 100 times of each other, and three orders of magnitude would be within 1000 times of each other, and so on with a power of 10 scale. Thus, in one example, a maximum cogging torque of 11 Nm which is within less than 10 times a total torque of 12 Nm would be within "the same order of magnitude" as each other because the total torque is 1.09 times that of the maximum cogging torque.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Cogging-Torque Actuator

FIG. 1A illustrates a cogging-torque actuator (CTA) 100 that is designed to maximize cogging torque, and that combines predesigned motion step with inherent compliance, impedance control, and torque sensing about a stable resting point of that step, as further detailed below. The CTA 100 can be considered an electromagnetic actuator for non-continuous rotation, and which can be incorporated with a joint module for a variety of uses, such as an actuator for a robotic joint, an exoskeleton joint, a prosthetic joint, or other joints or actuator mechanisms which can include passive mechanisms which operate in the absence of an electric current. By maximizing cogging torque, the CTA 100 does not spin continuously and is not intended to operate at high rotational speeds. Instead, a local controller can be implemented to control application of electrical fields applied to the CTA 100 (i.e., a control scheme for commutation of the CTA 100) that provides a compact, energy efficient electromagnetic actuator that is capable of acting as a spring, a clutch, a brake, and/or a load-bearing device, which dramatically reduces the complexity of a particular joint module of a robotic joint, for instance, or other suitable system, because of the size and low energy consumption characteristics of the actuator. These and other benefits and advantages should be appreciated from the following description and accompanying drawings.

Figure 1B:
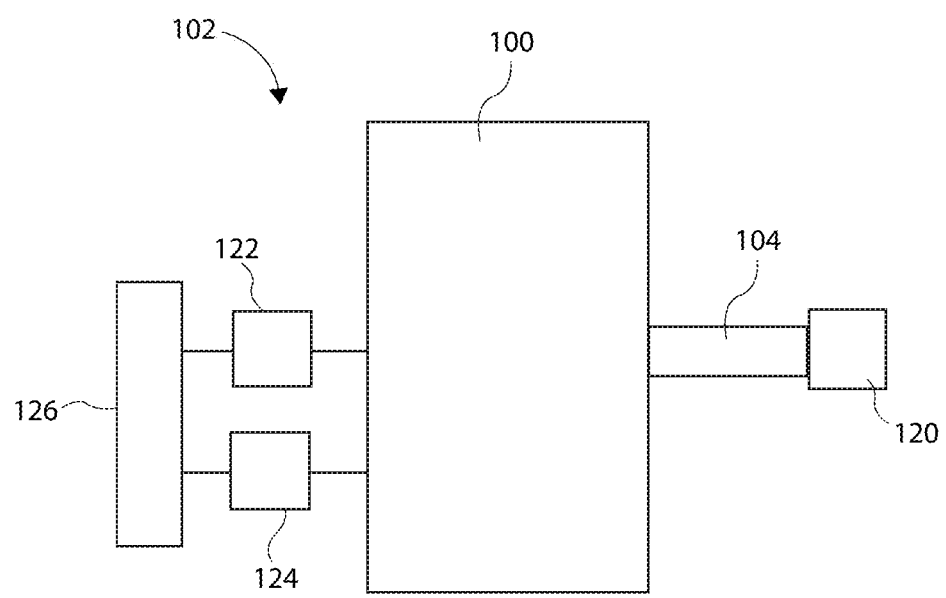
FIG. 1B illustrates a system for controlling rotational movement of a joint with the CTA of FIG. 1A, and showing a partial cross sectional view of the CTA, and including a schematic view of components for controlling rotational movement of the CTA in accordance with an example of the present disclosure.

The CTA 100 shown in FIG. 1A illustrates a slice of a larger/entire electromagnetic actuator. Note that FIG. 1B shows a block diagram of the CTA 100 of FIG. 1B, and also schematically illustrates other aspects or components of the joint module 102 that can incorporate the particular CTA 100 of FIG. 1A or other CTAs discussed herein. As an illustration, the CTA 100 can comprise an output shaft 104 rotatable about and defining an axis of rotation X, and a permanent magnet rotor 106 comprising north and south magnetic poles 108a and 108b attached to the output shaft 104. The north and south magnetic poles 108a and 108b can be curved magnets each formed radially in 180 degrees, and that collectively surround a portion of the output shaft 104. Notably, the north and south magnetic poles 108a and 108b can be shaped less than 180 degrees (FIG. 13A or other configurations including more than two rotor poles), or can be smaller linear segments, in some examples. Note that the output shaft 104 and the poles 108a and 108b may be considered collectively "a rotor" as used herein.

A stator device 110 (e.g., "stator") can surround the permanent magnet rotor 106, and can comprise a ferromagnetic pole body 112 that includes four ferromagnetic stator poles 112a-d each wrapped in a conductive wire 114a-d (e.g., the wrapped copper wires define stator coils around each stator pole). Note that four or more ferromagnetic stator poles can be incorporated, such as up to twelve or more, each wrapped in a stator coil. A housing structure 116 is attached to the outside of the ferromagnetic pole body 112. The outside surface of 116 can be smooth, corrugated, shaped with fins etc. for the purposes of encouraging cooling, thermal conduction, or mounting.

Notably, the ferromagnetic stator poles 112a-d are sized and spaced apart radially from each other (i.e., by slots where the stator coils are situated), and spaced from the permanent magnet rotor 106 by a gap G, in a configuration or arrangement that increases or maximizes the cogging torque of the CTA 100. As noted above, cogging torque is the torque due to the interaction between permanent magnets of a rotor and stator slots of a permanent magnet machine, such as a brushless motor. Such cogging torque is also known as detent or "no-current" torque. Cogging torque varies for each device configuration and is position dependent while its periodicity per revolution depends on the number of magnetic poles and the number of teeth on the stator. Notably, cogging torque is an undesirable component for the operation of traditional electromagnetic motors because it causes energy losses and jerkiness in rotational movement, particularly at low rotational speeds. Cogging torque results in reverse torque as well as speed ripple, and therefore cogging torque is traditionally minimized in a particular motor design for purposes of efficiency and smooth rotational movement. See, for example, Bianchi and Bolognani, *Design Techniques for Reducing the Cogging Torque in Surface-Mounted PM Motors*, IEEE Transactions on Industry Applications, Vol. 38, No. 5 (2002) which is incorporated by reference herein.

However, the CTAs contemplated in the present disclosure, including CTA 100, are designed to maximize cogging torque, which has desirable effects under certain applications, such as for smaller rotational movements required to effectuate movement of robotic joints. In a specific example, a particular CTA can have a defined maximum cogging torque of 11 Nm and a minimum total torque of 12 Nm when using a maximum allowable current density, where the total torque includes the cogging torque plus an electromagnetic torque. Such an arrangement will be able to passively hold a load of 11 Nm and ensure at least 1 Nm (for instance) to move the load, as defined by a design of the CTA (see below for a discussion of design parameters for CTAs). Therefore, the minimum total torque (12 Nm) of the CTA is "within the same order of magnitude" as the maximum cogging torque (11 Nm), because 12 Nm is 1.09 times that of 11 Nm.

As noted above, traditional electromagnetic motors (such as brushless motors for continuous rotation) are designed to minimize cogging torque, because it is an undesirable torque resistance for continuous rotation of the motor, and therefore affects efficiency of the motor. Thus, in one specific example, a traditional electromagnetic motor may have an electromagnetic torque of 50 Nm and maximum cogging torque of 0.25 Nm, which results in a minimum total torque of 49.75 being approximately 200 times than that of the maximum cogging torque of 0.25 Nm, in this example. Here, as with many traditional electromagnetic motors, the total torque and maximum cogging torque are at least two orders of magnitude away from each other, and therefore are never within "the same order of magnitude" as each other.

In one example, and with reference to FIG. 1B, the joint module 102 can comprise the CTA 100 having the output shaft 104 coupled to a transmission 120 for gearing down (or up) the rotational output transferred by the output shaft 104 to the transmission 120 (or the output shaft 104 can be directly coupled to a support member for rotation thereof on a 1:1 ratio). The transmission 120 can comprise capstan cable drives, magnetic gears, planetary transmissions, and other suitable geared systems or components. The transmission 120 can be useful to gear down the rotational movement of the output shaft, because each step of the motor may be 45 or 90 degrees, for example, and in applications where the degree of rotation required may be 20 degrees or less, the transmission can assist to achieve this by gearing down the rotation of the output shaft 104. Regardless, any number of transmission units can be coupled to the output shaft to achieve a desired motion.

The joint module 102 can further comprise a controller 122 operably coupled to the conductive wires 114a-d for controlling an electrical field or current applied to one or more of the conductive wires 114a-d (i.e., opposing conductive wires or stator coils in a commutation operation). The joint module 102 can further comprise sensor(s) 124, such as Hall effect sensor(s) and encoder(s), associated with the permanent magnet rotor 106 (or the output shaft 104) for determining the angular position and velocity of the permanent magnet rotor 106 relative to the stator. The joint module 102 can further comprise a central processing unit (CPU) 126 having one or more processors operably coupled to the sensor(s) 124 and the controller 122 for processing data and generating commands for the controller 122 to execute, such as the amount of current, polarity, and commutation scheme for particular opposing stator coils. A power supply (not shown), such as a battery or DC power supply, can be electrically coupled to (or part of) the joint module 102 for powering the components thereof. Thus, the joint module 102 and the CTA 100 enable inherent torque sensing capability where the stiffness function of the CTA 100 is known or determined. Because of the inherent link between position (determined by sensor(s) 124), stiffness (known based on the design parameters), and stator currents (known as applied), the torque on the permanent magnet rotor 106 can be deduced from the encoder information, embedded Hall-effect sensors, and knowledge of applied stator currents. Note that the CPU 126 can be located adjacent to or remotely from the CTA 100, and therefore wirelessly communicatively coupled to the sensor(s) 124 and the controller 126 via suitable known means.

Figure 2A:
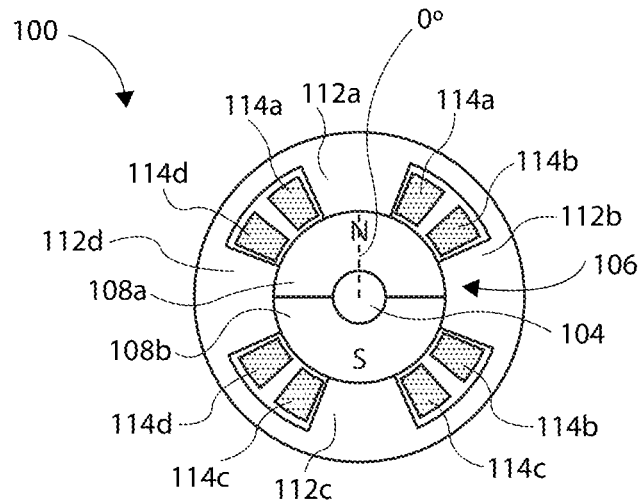
FIG. 2A is a 2D schematic of the CTA of FIG. 1A at a stable position of minimum (zero) cogging torque.
Figure 2B:
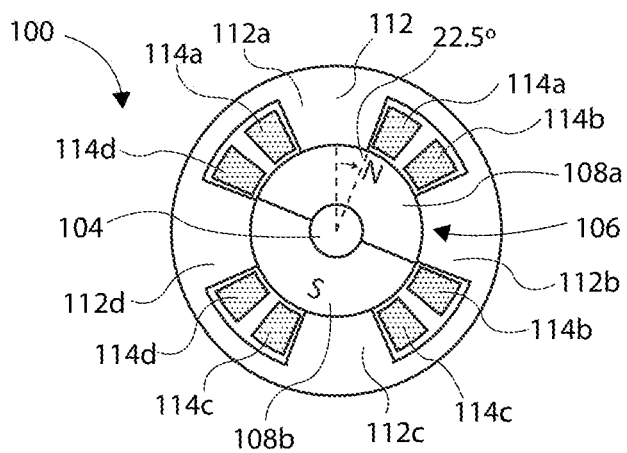
FIG. 2B is a 2D schematic of the CTA of FIG. 2A at a position of maximum cogging torque with rotor at 22.5 degrees rotation relative to a stator device.
Figure 2C:
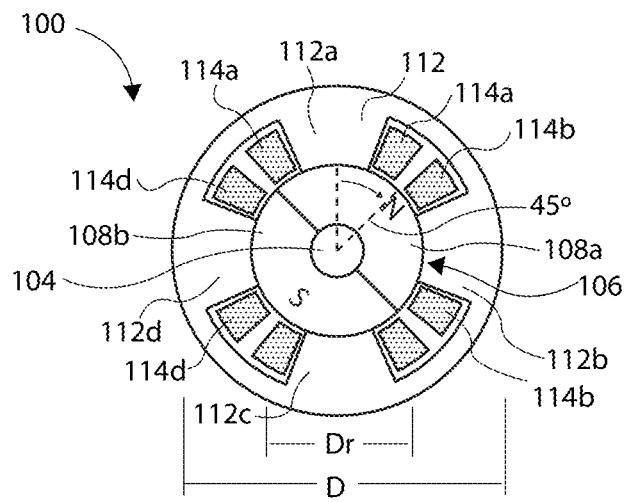
FIG. 2C is a 2D schematic of the CTA of FIG. 2A at an unstable position of minimum (zero) cogging torque with rotor at 45 degrees rotation relative to the stator device.

In one example of operation, FIGS. 2A-2C illustrate rotation of the permanent magnet rotor 106 (and output shaft 104) from a zero degree position (FIG. 2A), to a 22.5 degree position (FIG. 2B), and to a 45 degree position (FIG. 2C). Thus, having two magnetic (rotor) poles 108a and 108b, and four stator poles 112a-d, the CTA 100 has a stepping resolution of 90 degrees and a 3 step commutation. Note that at the zero degree position of FIG. 2A, the CTA 100 has a minimum (zero) cogging torque, meaning that the permanent magnet rotor 106 is experiencing a stable passive equilibrium by virtue of magnetic force. In response to applying an electrical field to conductive wires 114b and 114d (i.e., opposing stator coils) in order to attract the north pole of the rotor toward stator 112b, and optionally applying an electric field to wires 114a and 114c in order to repel the north pole of the rotor toward stator 112b, a generated electromagnetic field causes rotation of the permanent magnet rotor 106 to the position of maximum cogging torque at 22.5 degrees of rotation relative to the stator pole 112a. The applied electrical field to the conductive wires 114b and 114d, and optionally 114a and 114c, can be sufficient to overcome the maximum cogging torque of the CTA 100 at that position, so that the permanent magnet rotor 106 can be caused to rotate through the unstable position of minimum (zero) cogging torque at 45 degrees relative to the stator pole 112a. Thus, the permanent magnet rotor 106 can be caused to get over "the hump" of the maximum cogging torque to rotate beyond the 22.5 degree position, at which point the electrical field can be reduced from the conductive wires 114b and 114d, and optionally 114a and 114c. At the 45 degree position, any applied electrical field can be removed from conductive wires 114b and 114d, and optionally 114a and 114c, or the electric field can be reversed to regenerate energy from the conductive wires. The stator pole 112b can "pull" the permanent magnet rotor 106 to a stable passive equilibrium position at approximately 90 degrees from the starting position of FIG. 2A. These operations can be repeated so that the permanent magnet rotor 106 can be stepped to various desired positions about the stator poles 112a-d. Although the process described above was described as having three distinct steps in the commutation process, the electric field applied to the stator coils can be varied in a continuous fashion to execute the commutation.

Further to this concept of stepping from stator pole to a neighboring stator pole, a negative electrical field can be applied to selective electrical coils to reverse the rotational direction of the permanent magnet rotor 106 as desired. For instance, once the permanent magnet rotor 106 is rotated to the 45 degree position of FIG. 2C, a negative electrical field can be applied to conductive wires 114a and 114c, and optionally to 114b and 114d, to generate the opposite electromagnetic field that causes counterclockwise rotation of the permanent magnet rotor 106 with the assistance of the cogging torque, which causes the permanent magnet rotor 106 to return to the stable passive equilibrium of FIG. 2A. Such clockwise rotation, and then counterclockwise rotation, of the permanent magnet rotor 106 in this manner can be useful with joint modules of robotic joints that requires short or small rotational movements in opposite directions, such as with exoskeleton joints, autonomous robotic joints, prostheses, etc. As noted above, a transmission coupled to the output shaft 104 can assist to gear down the rotation of the output shaft 104 to an output support structure. For instance, in non-limiting examples, the aforementioned zero to 45 to zero degree position movements can be geared down 3:1, 4:1, or even 20:1 by a suitable transmission or gear train, for instance.

The stable passive equilibrium achieved at the zero point position of FIG. 2A is advantageous because it requires zero electrical energy to maintain this position under a torque load applied to the output shaft 104 because of the passive magnetic field between the rotor and stator. With traditional electromagnetic motors, a large amount or maximum amount of electrical energy must be applied to some or all stator coils of the motor in order to "hold" a load in place using the motor, which makes the motor run hot and inefficient. Other means of holding a load in place include incorporating a brake mechanism, as noted above, which adds to the complexity of a joint module, as well as the control aspects. In this way, traditional motors require electrical energy or brake mechanism to support a load because the very small cogging torque (that was minimized on purpose) is not sufficient enough to resist a typical load or payload that may need to be lifted and/or held in place by a robotic arm, for instance.

However, with the CTA 100 being at the zero position of FIG. 2A, assume the maximum cogging torque is 11 Nm, which means that a torque load of less than 11 Nm can be held via the output shaft 104 without supplying any electrical energy to the conductive wires 114a-d of the CTA 100 (and without incorporating a brake mechanism). This is because of the inherent or passive magnetic force generated between the permanent magnet rotor 106 and the stator pole 112a that "holds" the output shaft 104 in place to resist torque loads of under 11 Nm. In this way, a magnetic spring exists that tends to pull or stretch a torque load back to the zero point. For instance, if a 3 Nm torque load were applied to the output shaft 104 (whether clockwise or counter clockwise), the permanent magnet rotor 106 may rotate the appropriate direction a few degrees, such as +/− 5 degrees from the zero point because of the magnetic force between the rotor and stator, depending on the particular design of the CTA 100. Yet the CTA 100 would resist this 3 Nm torque load via passive stable equilibria due to said magnetic force, thereby holding it in place and supporting the load, all without requiring any electrical energy (and/or braking mechanism) to hold the load. This provides a very efficient electromagnetic motor in a compact form that utilizes magnetic force as a holding torque or "a brake", in a way.

Regarding the magnetic spring effect of a particular CTA, prior joint modules require the addition of a series elastic element, such as a pneumatic spring, coil spring, etc. that may selectively store and release energy, such as during gait movements or lowering loads. However, with a particular CTA, a magnetic spring effect is inherent to the CTA because of the design of the stator that provides a large cogging torque also has a natural or passive spring effect in either rotational direction from a stable or zero point. Thus, additional spring mechanisms, sensors, controllers, etc., are not required for the CTA to store and release energy via the magnetic spring effect described herein, although such mechanisms can optionally be used to augment or adjust performance for a particular application.

Figure 3:
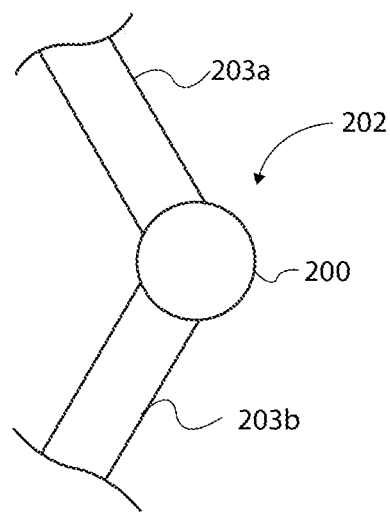
FIG. 3 shows a CTA incorporated in a joint of first and second support members in accordance with an example of the present disclosure.

FIG. 3 illustrates that the joint modules (having a CTA) contemplated herein can be incorporated with a joint rotatable about supported members. For instance, a joint module 202 (e.g., 102) having a CTA 200 (e.g., 100) can be coupled to a first support member 203a and a second support member 203b that are rotatable relative to each other about an axis of rotation. More particularly, the first support member 203a can be attached to an input member, such as structure 116 described regarding FIG. 1A, that is attached to a ferromagnetic stator body (e.g., 112) of the CTA 200. The second support member 203b can be attached to an output shaft (e.g., 106) of the CTA 200, or to a transmission coupled to the output shaft. Thus, the CTA 200 can be controlled to actuate the joint in the clockwise and/or counterclockwise directions, similarly as described above, and can be designed having 4, 6, 8, 10, or 12, or more, stator poles that define given steps of the rotor.

In one example of a particular application, an electrical field need not be utilized to operate the CTA 200 as a stepper hinge, such as for a window, door, etc. that can be moved to a new step position by a user, and then held in place by the passive magnetic force of the CTA (e.g., without applying any current). For instance, the CTA 200 can be designed to support a certain torque load on the first support member 203a, such as the weight of a computer monitor or other device that requires support in a certain position. If the position of the monitor needs to be changed, such as raised upwardly, a user can push upwardly the monitor, which causes the permanent magnet rotor to rotate with a sufficient torque to overcome the maximum cogging torque of the CTA 200 to move the permanent magnet rotor to a next step position, and so on. Similarly, the monitor can be lowered by the user with sufficient force to rotate the permanent magnet rotor the opposite direction to overcome the maximum cogging torque to move the permanent magnet rotor to the previous step position. Thus, the stator coils, controller, etc., may not be necessary to operate the CTA 200 in this manner as a hinge device.

In this way, the CTAs contemplated herein can operate as a clutch, such as a movable brake, because without any current applied the CTA can allow a small step in one direction upon a force to move to a new region of stable attraction of the CTA. For instance, where you want to control the resistance to motion, such as from a minimal force of a human or object, the CTA may rotate to the next step, thereby moving away a support structure coupled to the CTA. Non-limiting examples of such passive CTA applications can include door hinges, monitor supports, lighting armatures, and the like.

Figure 4:
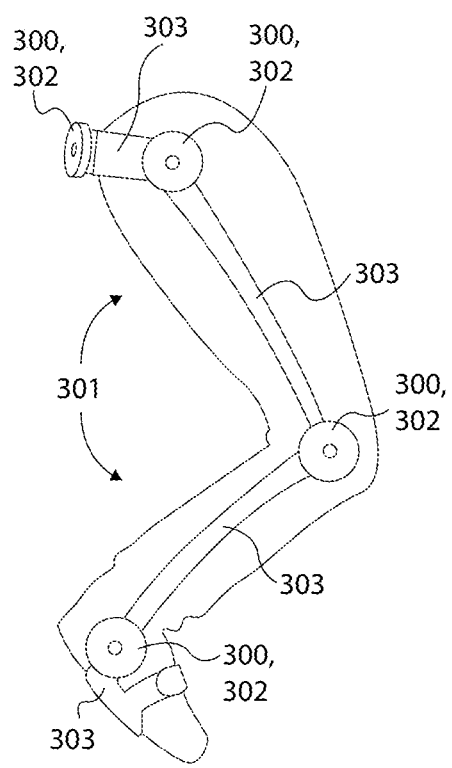
FIG. 4 shows a lower body exoskeleton including a plurality of CTAs incorporated in joints of the exoskeleton in accordance with an example of the present disclosure.

FIG. 4 illustrates that the joint modules (having CTAs) contemplated herein can be incorporated with an exoskeleton 301, such as the lower body exoskeleton shown, and/or with an upper body exoskeleton (not shown). Specifically, a plurality of joint modules 302 (e.g., 102) each having a CTA 300 (e.g., 100) can be coupled together by a plurality of robotic support members 303, and that define a plurality of degrees of freedom that correspond to degrees of freedom of human joints (e.g., medial/lateral and/or flexion/extension of the ankle, knee, and hip joints). A central computer system (e.g., in a backpack not shown) can be operatively coupled to each of the joint modules 302 to process collected data from sensors regarding the position, velocity, and torque associated with each joint module 302. A CPU of the computer system can then process the data and transmit command instructions to each joint module 302 to control the position and rotational velocity of each CTA 300 of each joint module 302, such as by utilizing the commutation schemes discussed herein. Thus, for a typical gait cycle while walking, the joint modules 302 can be individually controlled to be actuated by application of an electrical field, such as during the extension phase of a particular joint. In other applications, such as when crouching down to pick up and lift a load (which may be a better use of CTAs having high cogging torque), the joint modules 302 can be individually controlled to overcome cogging torque to move from step to step of each CTA, as appropriate, so that the individual can crouch down by virtue of the weight of the individual. Then, once the load is picked up by the individual and the individual begins to stand up (and the sensors sense such movement), one or more of the joint modules 302 can be actuated by applying an electrical field to apply a torque to assist lifting the load with the individual. Advantageously, while a wearer is holding the load and standing, all or some of the CTAs can be moved to their passive stable equilibria positions (zero point) so that no electrical energy or brake is required to support the weight of the exoskeleton, the wearer, and the load held by the wearer. Thus, depending on the task, the joint modules 302 can be controlled to apply particular torques in particular directions to achieve the desired task.

The same or similar holds true for tasks associated with an upper body exoskeleton having a plurality of joint modules. Further to this example, assume a CTA (e.g., 100, 400, 500) is incorporated in an elbow joint of a robotic arm (whether of an exoskeleton or a robotic arm/system), and is designed to "hold" a certain load in place, such as 11 Nm exemplified above. If a first payload were held by the robotic arm, equivalent to a 4 Nm torque load to the CTA, the output shaft of the CTA would slightly rotate a certain degree (e.g., 6 degrees downward) because of the aforementioned magnetic spring effect of the CTA, but the robotic arm would support the payload without application of electrical energy or operation of a brake mechanism. If a second (similar) payload were added to the first payload, thereby exerting another 4 Nm torque load for a combined torque load of 8 Nm for both payloads, the output shaft of the CTA would again rotate (e.g., an additional 8 degrees downward because of the nonlinear magnetic spring effect), but the robotic arm would still support both payloads without application of electrical energy or operation of a brake mechanism. This is similar to the motion primitives that exist with human elbow joints when supporting progressive loads, as further discussed below. If a third (similar) payload were added to the first and second payloads, thereby exerting another 4 Nm for a combined total torque load of 12 Nm, then the CTA would move one step from one stator pole to the next stator pole, because the 12 Nm torque load is enough has overcome the maximum cogging torque of 11 Nm of the CTA. Thus, the robotic arm may drop or lower the payloads a certain degree, which could be sensed by the sensors, and then the controller can be controlled to apply an electrical field to a set of coils to cause opposite rotation of the output shaft (i.e., step up the CTA) to support the addition load held by the robotic arm, or apply an electrical field sufficient to move the arm back to its original step position to support the load.

This, and other similar applications, provides a "safe" robotic system and operating environment, because the robotic arm would not be "too strong". Rather, it would act more like a human arm, having limited lifting capabilities and spring-like joints that may deflect or be compliant to a certain degree in response to a threshold torque load applied to or against the robotic arm. For instance, if a robotic arm (or leg) accidentally impacts a wall or other structure, the robotic arm would not necessary damage the wall or itself, because the CTA joints of the robotic arm would somewhat deflect or spring backwards upon experiencing too high of a torque load to the joints because of the aforementioned spring effect and stepping motion of the permanent magnetic rotor relative to the stator poles. However, such a robotic arm could be as fast and strong as similar robotic arms, yet have this compliance and flexibility due to the inherent characteristics of the CTAs described herein. Such configuration can eliminate the complicated sensors, back driving, and control schemes required of other robotic arms that must "sense" such impacts and respond accordingly by controlling the position and velocity of the robotic joints of an arm (and at a high energy cost) to avoid damage to a structure or injury to a person, for instance. Thus, the CTAs contemplated herein have an inherent safety factor, while being compact and energy efficient to operate. Thus, the CTA described herein can be used in a wide variety of electrically driven applications including, but not limited to, robotic joints, precision actuators, manufacturing automation equipment, haptic interfaces, and the like.

With continued reference to the example of FIGS. 1A-2C, the controller 122 is operable to implement one or more bioinspired motion primitives associated with rotational movement of the rotor relative to the stator. Specifically, the bioinspired motion primitives can be managed or controlled locally (at or near the CTA 100) by the controller 122 that implements control policies. Such bioinspired motion primitives include control of: 1) mechanical impedance; 2) point-to-point submovements, and 3) oscillations. Note that these three fundamental motion primitives are used by humans, as noted above. Each of these three submovements can also be implemented by the CTA 100, which can enable improved agility by alleviating some of the direct feedback control tasks of a high-level controller that would typically be utilized to control traditional robotic joint mechanisms.

Figure 5:
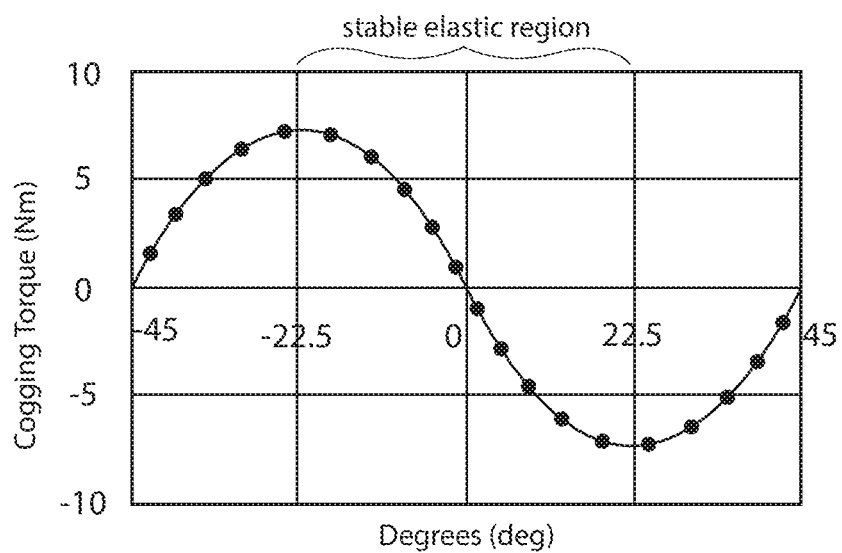
FIG. 5 is a graph showing simulated cogging torque versus relative angle between rotor and stator for the CTA of FIG. 1A.

Regarding control of mechanical impedance as depicted FIG. 5, the cogging torque binding the permanent magnet rotor 106 to a given stator pole serves as a magnetic spring, as also discussed above. This magnetic spring is nonlinear (e.g., a softening spring), but it may be approximated by a linear spring for a substantial portion of the range of the spring. This spring stiffness is innate or inherent to the CTA 100, and requires no power consumption, as also discussed above. In one example, the CTA stiffness in both the positive and negative direction can be modified dynamically by supplying a current through the appropriate conductive wires associated with the position of the permanent magnet rotor 106. The change in CTA stiffness can be approximately linear with respect to the amount of current supplied, whereas the power consumption can be quadratic with respect to current, leading to the quadratic power-versus-stiffness curve shown in FIG. 9B. As a result, from an energy-efficiency perspective, it can be desirable to command stiffness values that are at or near the passive stiffness of the particular CTA. For example, stiffness can often be within 100% of the passive stiffness.

Figure 9A:
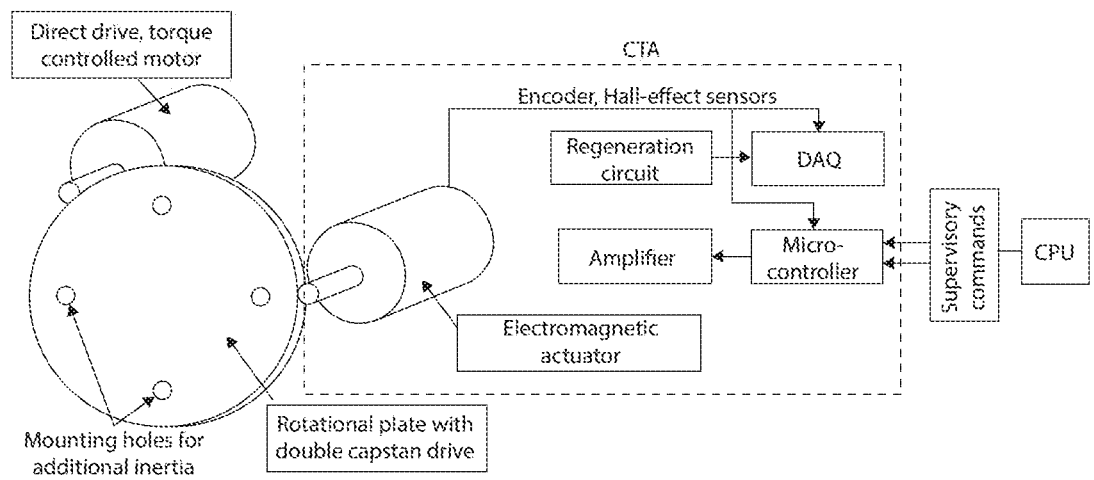
FIG. 9A is a schematic drawing of a CTA benchtop test setup in accordance with an example of the present disclosure.
Figure 9B:
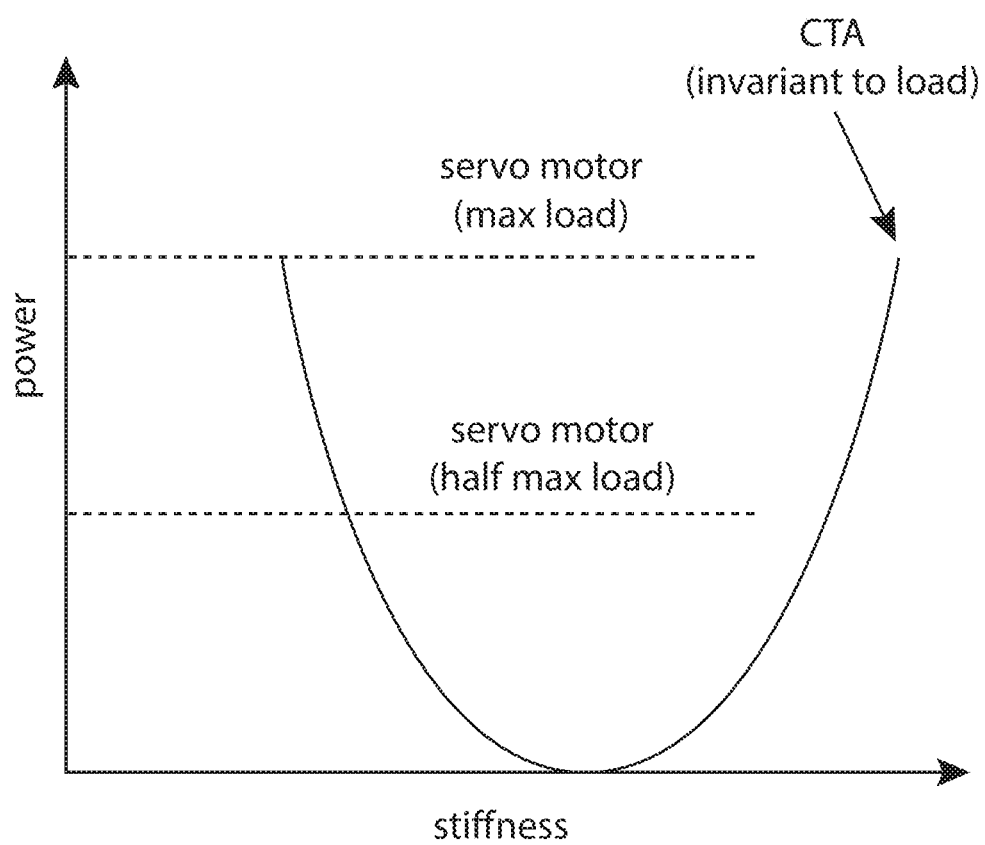
FIG. 9B is a graph of power versus stiffness for a CTA and a servo-controlled motor exerting a torque load onto the CTA of FIG. 9A in accordance with an example of the present disclosure.

When comparing control of stiffness with the CTA to a traditional back-drivable motor (with or without gearing), impedance control is traditionally accomplished by closing a proportional-derivative position servo loop around a position set-point, where the proportional gain serves as the stiffness. Like any digital closed-loop control system, there will be an upper limit on the stiffness that can be stably implemented (and that upper limit can be relatively low for traditional motors without significant gearing). In contrast, the CTA examples of the present disclosure can be operable to control stiffness directly in an open-loop fashion (i.e., constant currents in the conductive wires around the stators), so there would be no or negligible stability issues. Rather, limits are present on the range of stiffness that can be rendered for a particular CTA. Considering the electrical power required to hold a load with a traditional back-drivable motor, the power is invariant to the stiffness of the servo controller. This is due to the fact that the load will reach an equilibrium in which the motor is exactly balancing the load; the stiffness being rendered only affects the position of that equilibrium. Thus, the power consumed is approximately linear with respect to the load, as shown in FIG. 9B. In contrast, the power consumed by the CTAs of the present disclosure is invariant to the load, as also shown in FIG. 9B. Thus, the (linearized) stiffness of the CTA is a function of the CTA's system parameters as well as the current through the stator coils. The inverse of this can be implemented in the CTA's local controller, such that the controller only receives high-level commands of the desired stiffness to be achieved.

Note that impedance is more than stiffness of a particular CTA, because damping is a contributor to the natural dynamics of the CTA. In the case of the servo-controlled traditional motor, damping is implemented using the derivative gain, and it is simple to peg the damping to the stiffness to achieve some desired property (e.g., critical damping). In the CTAs contemplated herein, there is an inherent damping effect due to friction in bearings and eddy currents that exist. This damping can be changed by implementing a local feedback controller. Unlike the stiffness controller, the damping controller is not trivially stable, so the stability of the damping controller can be analyzed as a function of the local controller's sampling rate.

In a specific example, FIGS. 8A-8E are graphs that illustrate ankle gait-cycle data, and specifically for a typical 90-kg human over-ground walking. The graphs show a peak torque of 147 Nm, a peak angular velocity of 219 deg/s, and a peak power of 303 W. Based on such data, a particular CTA of a joint module associated with rotation of an ankle joint (e.g., exoskeleton flexion/extension ankle joint), the range of impedances a designed CTA can render throughout the gait cycle would be 36-570 Nm/rad for stiffness, and 0.9-2.2 Nms/rad for damping.

Regarding the second motion primitive of control over point-to-point submovements, it should be noted that when humans move a limb from one point to another (e.g., in a straight line), it is not actually accomplished as a single movement, but is actually accomplished by stringing together a number of smaller submovements. Biology has its own reasons to "choose" the duration of its submovements, but with the CTAs contemplated herein the natural smallest division of movement is the rotor moving from one stator pole to the next neighboring stator pole. In a sense, human submovement is close to commutation in traditional motors (e.g., stepper motors), although it is fundamentally different to realize. Note that such a submovement also ties in with the impedance discussed above, since a point-to-point submovement should naturally end with an impedance command.

For quasistatic stepping, and even more so for dynamic motion, it would be suboptimal to establish a one-size-fits-all stepping event. The stepping event can either be informed by the load on the actuator (which can be estimated locally) in the case of an open-loop stepping event, or the stepping event can be constructed as a closed-loop control policy that inherently takes the applied load into account. To illustrate the importance of incorporating knowledge of the load (not only for energy efficiency, but also for basic functionality), consider a particular CTA that is loaded in the direction of the intended step. The "future" neighboring stator pole (e.g., moving from stator pole 112a to 112b of FIG. 1A) can be attractive to initiate a step, but the "present" stator pole (e.g., 112a) would be repulsive. Considering a CTA that is loaded against the direction of the intended step, both the "present" and the "future" stator poles can be attractive to initiate a step, but at some point the "present" stator pole will transition to being repulsive. The CTAs contemplated herein enable inherent torque sensing capability based on a known stiffness function. Because of the inherent link between position, stiffness, and rotor currents, the torque on a particular permanent magnet rotor can be deduced from encoder information, embedded Hall-effect sensors, and knowledge of rotor currents, as also discussed above.

Parameterizing dynamic stator-current pulse trajectories can be implemented with a particular CTA to accomplish a single step from one stator pole to the next, with the permanent magnet rotor starting and stopping at rest proximate respective stator poles. An open-loop trajectory can be developed based on the design of the particular CTA and a known load, and a closed-loop control policy can be implemented to the control the CTA (which can also include model-based feedforward terms). The dynamics can be optimized for energy efficiency, first assuming no regeneration, and then assuming regeneration of the CTA. The most energy-efficient stepping event can take some specific duration of time, and can have associated mean and peak velocities. By incorporating the ability to specify the desired duration of the stepping event, one can evaluate the effect on energy consumption. Since it is known that humans move their limbs with minimum-jerk trajectories (which are well modeled by fifth-order polynomials), optimization cost functions can penalize jerk. The robustness of the submovement controller to uncertainty in the CTA is also a consideration, as well as uncertainty in the estimated load on the CTA.

The controller (e.g., 122) of a particular CTA accommodates the high-level command to "take N steps over T seconds". Note that it may be insufficient to simply string together N single-step events, since the intermediate events can capitalize on the momentum in the rotor to hand it off from one stator pole to the next stator pole. Knowledge of the effective rotor inertia and any applied loads can be considered in the controller to effectively realize the goal of energy efficiency. Therefore, dynamic models and the local controller can be designed in order to implement higher-level supervisory control commands in an energy-efficient manner. Again, both open-loop stator-current trajectories as well as closed-loop control policies are considered in such control commands. The general N-step controller may be essentially invariant for all N>1 commands—comprising a start pole, and end pole, and an arbitrary number of intermediate poles—or if the energy-efficient dynamics are different for each N>1. In one example, it may be useful to implement a controller that is invariant to N.

Regarding the third motion primitive of oscillations, this is a feature for typical robotic motions such walking, running, and repetitive hand motions. The CTAs contemplated herein have an advantage over traditional motors in implementing oscillations, because a CTA contains inherent passive stiffness properties (see the graph of FIG. 5). Thus, the local controller (e.g., 122) can receive a high-level oscillation command specifying a desired frequency and amplitude, and an initial phase within the cycle. Note that for many activities the exact frequency and amplitude may not be as important, such that the high-level command may instead specify a frequency and amplitude range. The local controller for a particular CTA can then control oscillations about a single stator pole, between adjacent stator poles, and between non-adjacent stator poles. As in the case of the impedance motion primitive, it can be beneficial to design a CTA with an end application, such that the passive stiffness and inertia of the CTA and any attached linkages result in a minimum-energy natural frequency close to application requirements. At the level of a traditional robotic joint, passive oscillation is sometimes implemented to improve energy efficiency. However, this integration occurs in a very application-specific way and entails collections of components added on to the actuator. By contrast, the CTAs contemplated herein have inherent behavior to enable energy-efficiency oscillations, because of the reduction in power to control the position and velocity of the CTAs, as compared to traditional continuous motors.

Figure 10A:
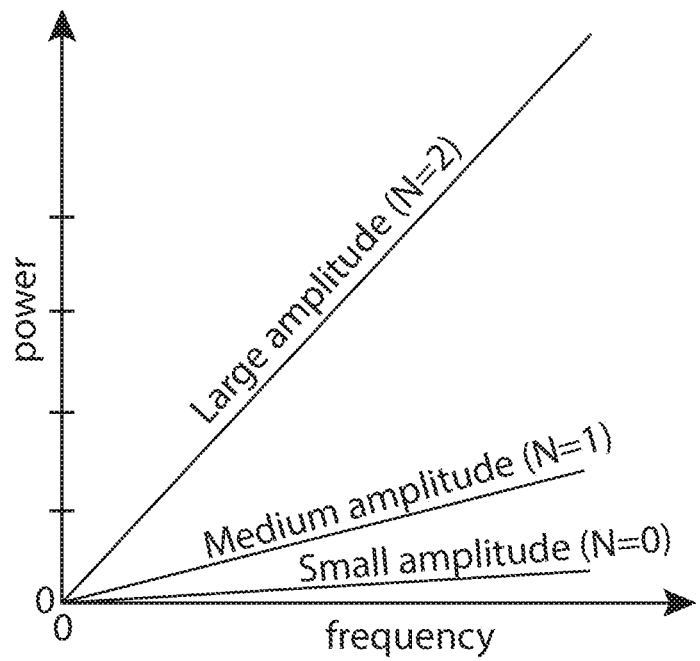
FIG. 10A is a graph of projected power versus oscillation frequency for a traditional electromagnetic motor.
Figure 10B:
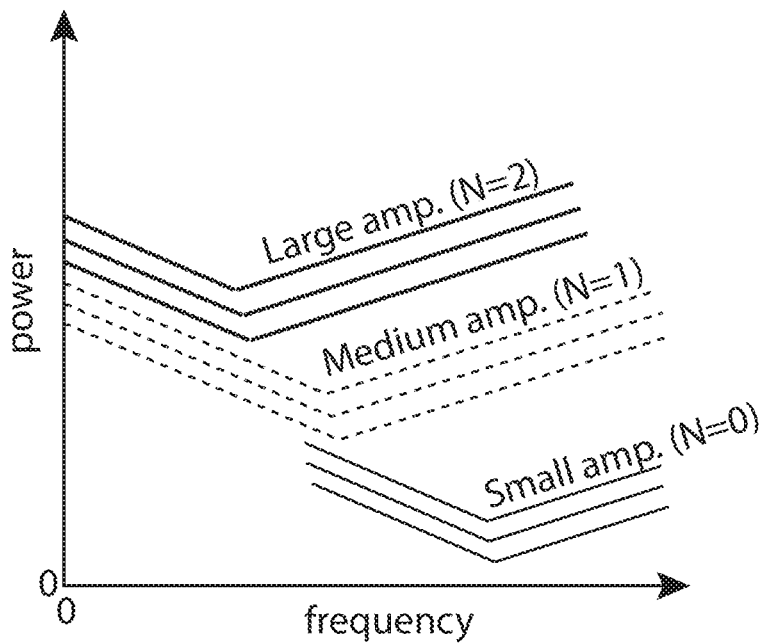
FIG. 10B is a graph of projected power versus oscillation frequency for a CTA for three velocity amplitudes, where N=0 corresponds to CTA oscillations about a single stator pole, and N=1 corresponds to CTA oscillations about adjacent poles, and N=2 corresponds to CTA oscillations between two stator poles removed by one intermediate stator pole, in accordance with an example of the present disclosure.

An oscillation motion primitive of a traditional electromagnetic motor is an active task in which the motor is commanded to follow a motion trajectory (e.g., sinusoidal). FIG. 10A shows the nature of the power required to implement an oscillation for varying amplitudes as a function of frequency of a traditional motor, and graphs three amplitudes: large, medium, and small. In the case of a particular CTA, FIG. 10B shows these same amplitudes as occurring about a single rotor pole (N=0), between adjacent stator poles (N=1), and between stator poles removed by one intermediate stator pole (N=2). An oscillation associated with N=2 would be roughly twice the amplitude of an oscillation associated with N=1. Note that FIG. 10A shows power as a function of the velocity amplitude ($|v|(j\omega)=\omega|x|(j\omega)$) because for a traditional motor, power scales linearly as a function of frequency for a constant velocity amplitude, and it scales cubically as a function of frequency for a constant position amplitude. For a given frequency, power scales as the square of velocity amplitude, which is also indicated in FIG. 10A. Note that the upper limit to the achievable frequency can be determined both by the inertia of the rotor and by stability considerations driven by the sampling frequency.

By contrast, the power required to create an oscillation primitive with a particular CTA, as shown in FIG. 10B, has a slightly more complex set of curves as compared to the data illustrated in FIG. 10A. First, there are multiple natural resonances within the CTA (e.g., N=0, N=1, and N=2). Consider the case for oscillations about a single rotor pole (N=0). At a given amplitude, there is a minimum-energy oscillation frequency. The only power required to maintain this oscillation frequency is the power to overcome friction and eddy current based damping. To move higher or lower in terms of frequency, the CTA can adjust its internal stiffness. As described above, the power cost to adjust stiffness scales with the square of change in stiffness. As oscillation frequency scales with the square root of stiffness $$\left(\text{i.e., } \omega = \text{?}\sqrt{\left(\frac{k}{m}\right)}\right),$$

the power required to move away from the CTA's natural oscillation frequency scales linearly with frequency. The maximum achievable frequency is limited by the rotor inertia of the CTA and sampling frequency of the local controller. For an N=0 oscillation, there may be a practical lower bound on the achievable frequency. If a slightly larger amplitude is desired, but one which would still occur about a single rotor pole, the power curve will shift slightly upward as more friction/damping energy will need to be overcome and some small level of stiffness control may need to be employed because the magneto-elastic stiffness is not linear. As the effective stiffness has the characteristics of a softening spring, an increase in amplitude would come with a small decrease in minimum-energy oscillation frequency. Thus the low point of the N=0 group of curves in FIG. 10B shifts slightly to the left for higher amplitude oscillations.

For a rotor of a particular CTA to oscillate between adjacent stator poles, the magneto-elastic potential energy peak between stator poles must be collapsed, as further detailed below. Thus, as shown in FIG. 10B, the set of N=1 and N=2 curves require more power than the set of N=0 curves. Furthermore, as N increases, the minimum-energy oscillation frequency decreases. For oscillations where N>0, the minimum achievable frequency should approach zero. Note that the y-axis (power) of FIGS. 10A and 10B are not the same, because a particular CTA consumes noticeably less power for almost any oscillation frequency-amplitude combination as compared to a traditional motor capable of similar torque output, because the CTA takes advantage of inherent internal compliance.

Therefore, in one example, where it is desirable to vibrate a member or object at a very high frequency, a particular CTA can be operated to vibrate by keeping the rotor within the boundaries of one stator pole, combined with the right phasing and amplitude. Thus, by applying a current through opposing stator coils to move the rotor a very small amount (e.g., less than 1 degree), and then removing the current so that the rotor springs back to or beyond its original position, and then quickly applying the same current again through the opposing stator coils (and then repeating this over and over), the attached member or object to the output shaft can vibrate at a very high frequency, which can be beneficial in a variety of applications, such as when using tools for tapping, hammering, stirring, etc.

Figure 11A:
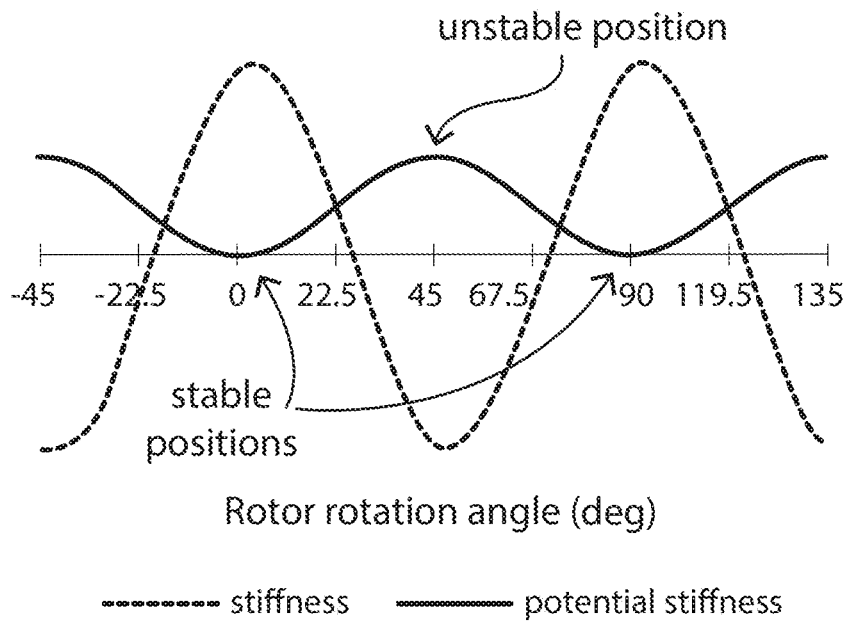
FIG. 11A is a graph of rotational stiffness and magneto-elastic potential energy for a CTA with 2 rotor poles and 4 stator poles, wherein the rotor poles and stator poles are aligned at 0 and 90 degrees, in accordance with an example of the present disclosure.
Figure 11B:
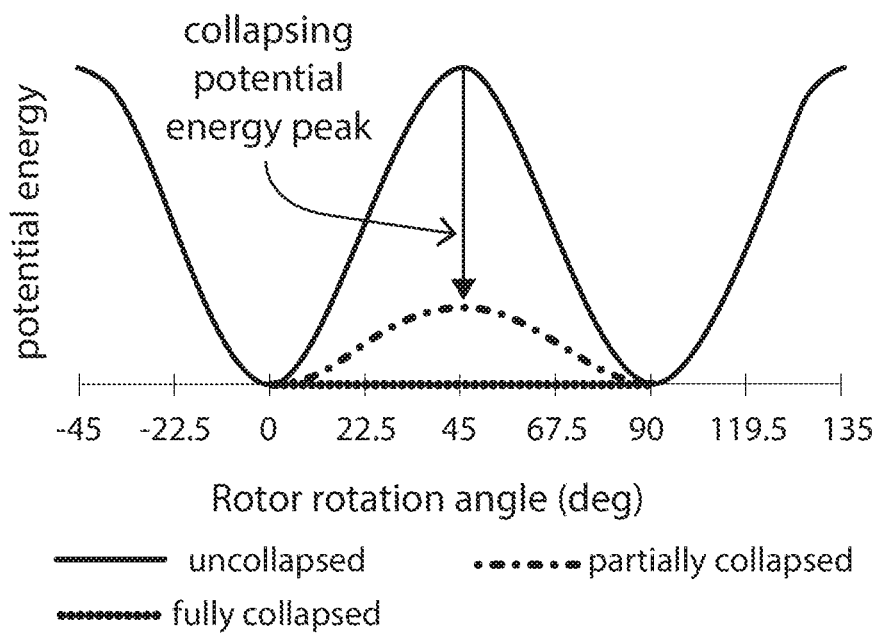
FIG. 11B is a graph showing unchanged potential energy function and potential energy functions with energy peak midway between stator poles collapsed to enable oscillation between two adjacent stator poles, in accordance with an example of the present disclosure.

FIG. 11A shows an example of stiffness vs. rotor angular rotation for a CTA with 2 rotor poles and 4 stator poles (i.e., FIG. 1A), and the associated magneto-elastic potential energy. The two energy wells correspond to the locations at which the rotor poles and stator poles are aligned. There is an unstable energy equilibrium between these two wells, which is the point at which the rotor is being magnetically pulled with equal force to each of the two stators. Oscillations can occur within a single energy well (i.e., within the capture range of a single stator pole). However, without active control, oscillations may not occur between adjacent stator poles because if the kinetic energy of the permanent magnet rotor and associated linkages is large enough to overcome the magneto-elastic energy peak, the permanent magnet rotor will just continue to rotate overcoming each successive energy peak. In order for the CTA to stably oscillate between adjacent stator poles, the magneto-elastic energy peak between the two poles must be collapsed using stator currents, but the energy peaks on either side of the two poles (i.e., not between them) must not be collapsed. This results in a potential energy function shape, as shown in FIG. 11B. Note that the energy peak need not be completely collapsed, but could be partially collapsed resulting in a bi-stable inter-well oscillation.

Figure 12:
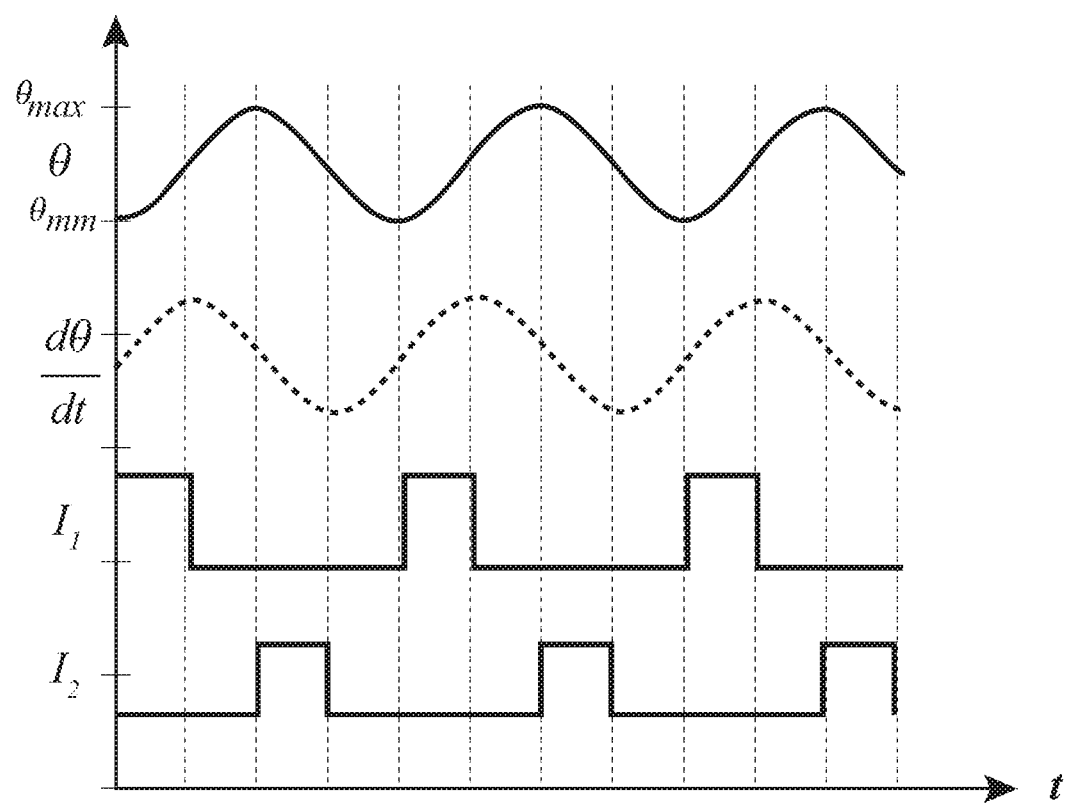
FIG. 12 is a graph of conductive coil current timing to support oscillation between adjacent stator poles, in accordance with an example of the present disclosure.

In regards to control over timing associated with a particular commutation scheme, the control currents supplied to one or more conductive wires or coils can be synchronized with both the (sensed) position and velocity of the permanent magnet rotor. FIG. 12 shows an example of the timing of the control currents for an oscillation between neighboring stator poles for two coils wound about the two stators (i.e., stator 1 and stator 2) (note that in FIG. 12, θ is the rotor angle, which oscillates between stator 1 and 2, and dθ/dt is the rotor angular velocity. $I_1$ and $I_2$ are the currents for stator poles 1 and 2, respectively). At time t=0, the rotor is aligned with stator 1 and is about to start moving toward stator 2. However, the stiffness from stator 1 will try to pull the permanent magnet rotor back to its prior position. A current pulse can be temporarily applied to stator 1 to counteract the magnetic attraction, allowing the permanent magnet rotor to move toward stator 2 (i.e., the stator current will collapse the magneto-elastic potential energy peak). This process can be repeated at stator 2 when the rotor is aligned with stator 2 and starting to move back toward stator 1. The encoder and Hall-effect sensors (FIG. 1B) can be used to determine rotor position and velocity. Note that it is possible to create the necessary stator current timing with an electrical oscillator, in which case the electrical pulses would be sinusoidal. This greatly reduces the energy cost to collapse the energy peak. The case in which oscillation will occur between non-adjacent stator poles is analogous. The only difference is that multiple energy peaks can be collapsed in sequence.

Referring back to FIG. 10B, power for the CTA can scale with velocity amplitude of the oscillation (i.e., how much more power the N=2 set of curves require than the N=1 set of curves). Consider the case in which the CTA is oscillating between adjacent stator poles (N=1). Then, a CPU can transmit a signal to the controller to command or instruct the CTA to increase amplitude such that the oscillation occurs between a stator pole and its second nearest neighbor (N=2). The fundamental difference between these oscillations is that two, instead of one, magneto-elastic energy peaks must be collapsed. Note that the power cost may then double, which would indicate linear scaling with oscillation amplitude. However, if the energy peak can be collapsed with an electrical oscillator, the power cost to do so may be smaller than the power to overcome friction. Thus, the increase in power, while technically increasing, looks more or less flat.

Note that a parameterized set of possible oscillations can be determined through modeling, and can represent information that can be shared with the high-level controller for a given robotic application. However, this reduced amplitude and frequency precision comes with vastly improved energy efficiency. This same sort of trade-off exists in biology. For example, although a human is able (through great effort) to walk at a relatively wide range of amplitudes and frequencies; they only choose to walk at a much narrower range of amplitudes and frequencies corresponding to energy-efficient gaits. Robots utilizing CTAs contemplated here will ultimately have similar traits.

A variety of factors are considered when designing a particular CTA to maximize or optimize cogging torque for a particular application. In one aspect, design can be done via finite element analysis using the factors described herein. For instance, the selection of the number of stator poles and rotor poles has an impact on the period of the cogging torque as the rotor moves from one stator pole to the next. The highest values of cogging-torque amplitude correspond to the lowest values of the period. This can be thought of as a motor in which multiple magnetic rotor poles align with stator poles simultaneously such that each rotor pole's torque vs. angular rotation is essentially in phase, so the contribution to cogging torque of each rotor pole accumulates. Higher period values correspond to designs in which the cogging-torque contribution of each rotor pole is unsynchronized. The period can be calculated and used to evaluate different configurations of stator poles and rotor poles.

$$NP = \frac{N_r}{HCF\{N_s, N_r\}} \tag{1}$$

Here, NP is the number of cogging-torque periods during a single rotation from one stator pole to the next, and $N_r$ is the number of rotor magnet poles (which must be even, e.g., $N_r=2$ corresponds to one north-south pair), and $N_s$ is the number of stator poles (which is equal to the number of stator slots), and HCF is the highest common factor.

The minimum period value from equation (1) is NP=1. Therefore, in order to maximize cogging torque, a rotor pole and stator pole combination that results in NP=1 should be selected. Example combinations include 2 rotor poles and 6 stator poles, 4 rotor poles and 8 stator poles, etc. (see e.g., FIGS. 13A and 14A).

The angle between stable equilibrium rotor positions is formulated by the following equation (1a):

$$\alpha = \frac{2\pi}{NP*N_s} \tag{2a}$$

where $\alpha$ is the mechanical angle between stable equilibrium rotor positions. As an example calculation, where $N_r$ 4, and $N_s$ 8, the following solutions are provided.

$$NP = \frac{4}{HCF\{8, 4\}} = \frac{4}{4} = 1$$

$$\alpha = \frac{2\pi}{1*8} = 0.785 \text{ rad} = 45 \text{ deg}$$

Thus, the angle between stable equilibrium rotor positions would be approximately 45 degrees. These calculations are correlated to the example discussed below regarding FIG. 14A.

Cogging torque as a function of rotor angular position ($\theta$) is defined in equation (3).

$$\tau_{cog}(\theta) = -\frac{1}{2}[\phi^2 \frac{dR}{d\theta}] \tag{3}$$

Here, $\phi$ is the airgap between the stator and the rotor, and $$\frac{dR}{d\theta}$$

is the change in reluctance with respect to rotor angular position. In order to maximize cogging torque, the reluctance R can change rapidly with respect to rotor position. Most designers try to minimize the change in reluctance through the geometry of the stator pole shoe, adding notches to the stator pole, or skewing stator poles. To maximize cogging torque, the airgap between stator and rotor can be minimized, and skewing and notches is avoided in the CTA exemplified herein. See, for example, FIG. 1A that shows a curvilinear configuration of stator poles adjacent the outer surfaces of the rotor poles, and which are devoid of skewing, notches, etc. that may traditionally be implemented in stator poles of existing motors. Additionally, stator pole shoe geometry can be selected to maximize cogging torque.

Figure 6A:
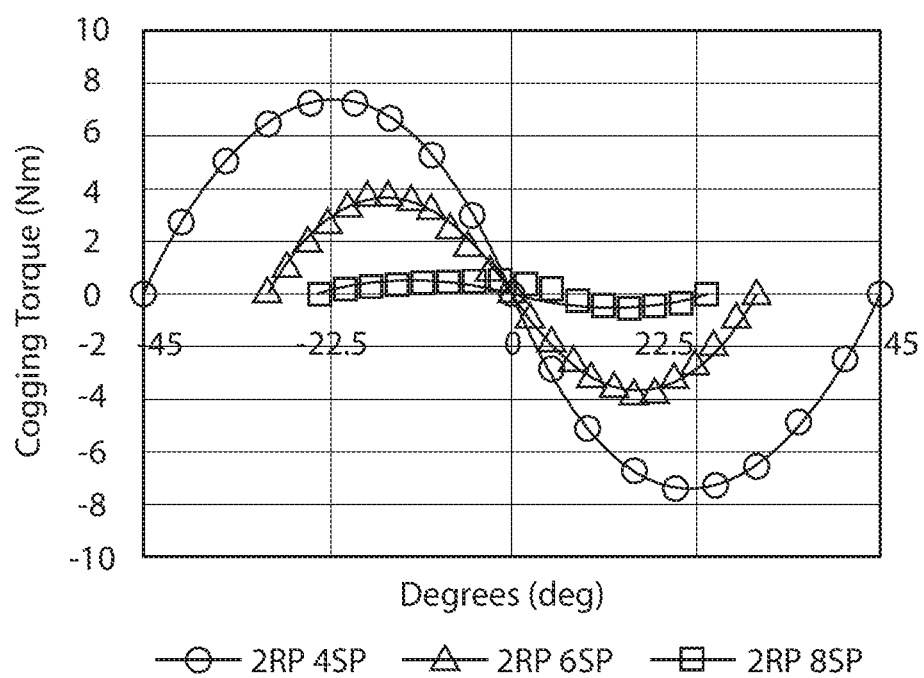
FIG. 6A is a graph of cogging torque versus angular position for three different CTAs having 2-rotor-pole (2RP) configurations in accordance with examples of the present disclosure.
Figure 6B:
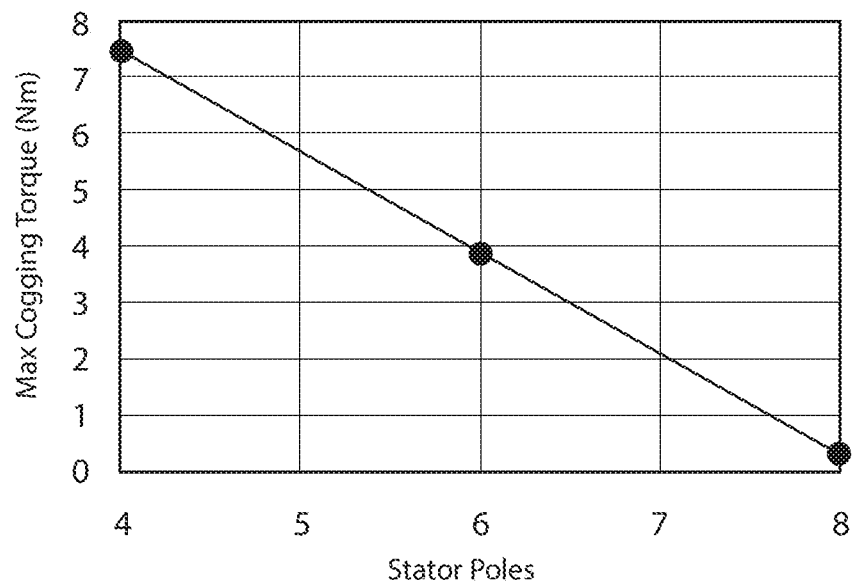
FIG. 6B is a graph of maximum cogging torque versus number of stator poles for a 2RP CTA in accordance with an example of the present disclosure.

FIG. 6A shows the data associated with cogging torque for three different CTA configurations each with 2 rotor poles (2RP), and one with 4 stator poles (4SP), and another one with 6 stator poles (6SP), and another with 8 stator poles (8SP), as labeled. The cogging torque is plotted for one period. As shown, the maximum cogging torque declines as the number of stator poles increases. Thus, the size of each stator pole decreases, as does the distance between stator poles. However, such decline or reduction provides a better stepping resolution: a 45 degree versus 60 degree versus 90 degree basic step for the 8SP versus 6SP versus 4SP stator. For example, FIG. 6B shows $\tau_{max}$ for a 2RP CTA versus number of stator poles and shows that $\tau_{max}$ relatively quickly decreases with an increasing number of stator poles. Note that the maximum cogging torque with a 4SP CTA is about 22 times larger than a 8SP CTA, and after gearing by a factor of 2 to match the stepping resolution of the 8SP CTA, the geared 4SP CTA would have a maximum cogging torque that is about 44 times that of the 8SP CTA. This can indicate that an optimal CTA configuration for this example would be to minimize the number of stator poles, while being consistent with equation (1), and use a high gear ratio.

Figure 7:
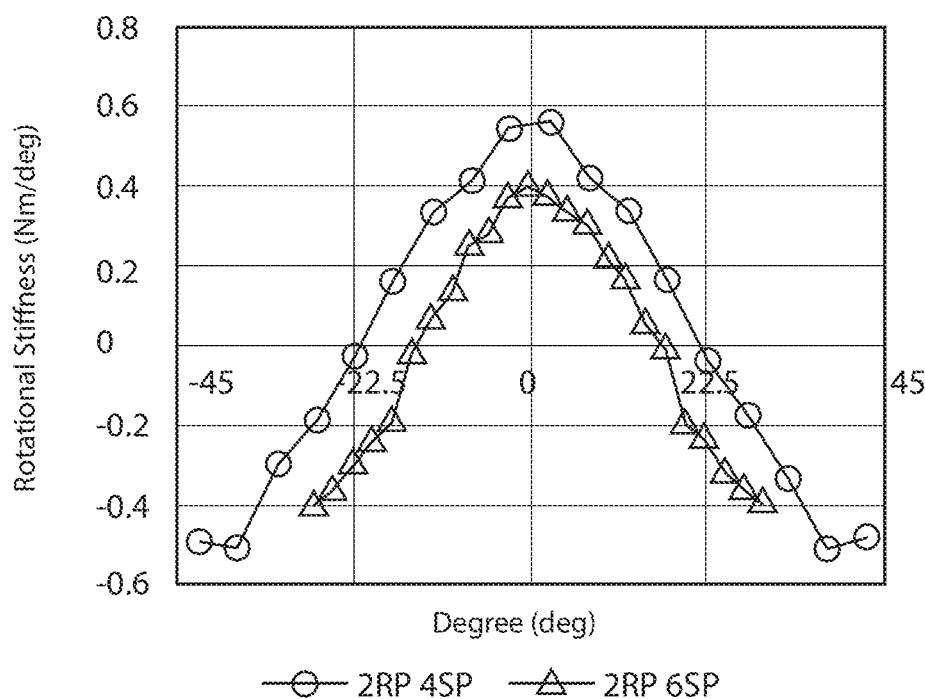
FIG. 7 is a graph of angular stiffness for two CTA configurations: 2RP-4SP, and 2RP-6SP, in accordance with examples of the present disclosure.
Figure 8A:
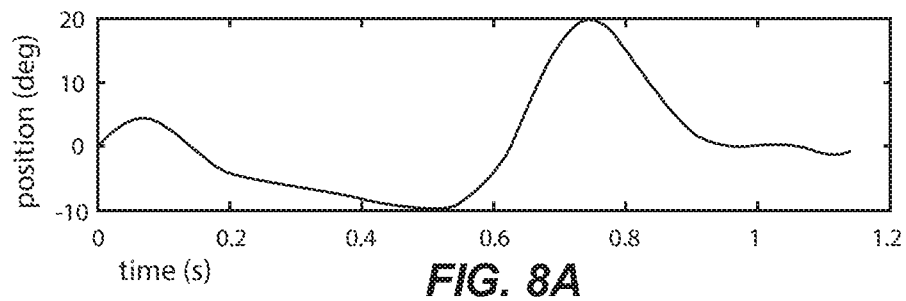
FIG. 8 includes a variety of graphs showing ankle data results for one gait cycle of a 90-kg individual walking over level ground at a normal pace in accordance with an example of the present disclosure.
Figure 8B:
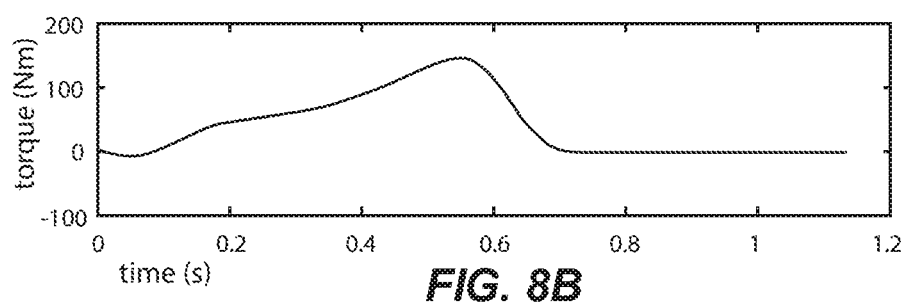
Figure 8C:
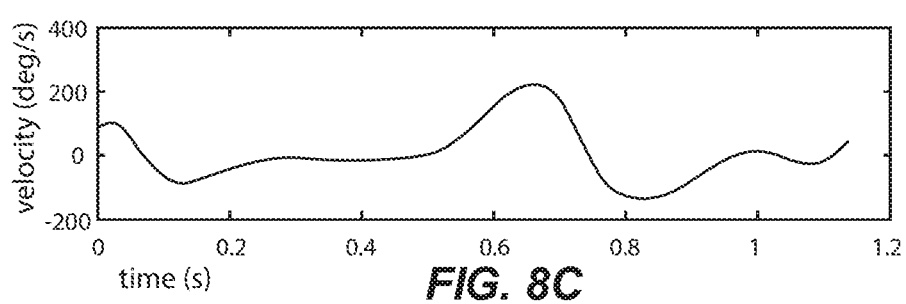
Figure 8D:
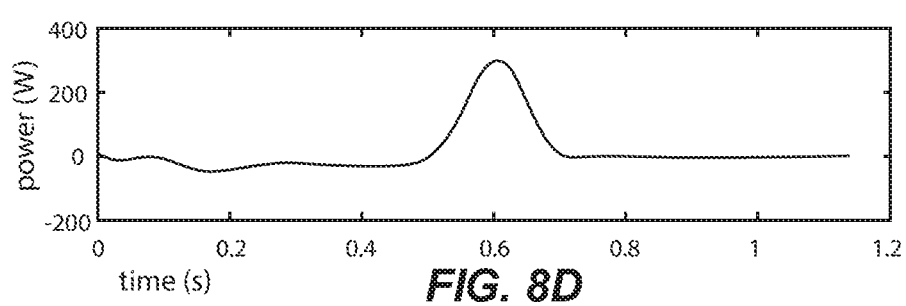
Figure 8E:
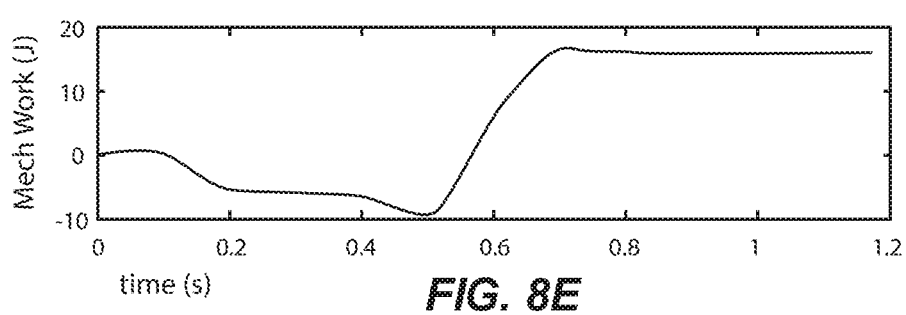

The data in FIG. 6A can be converted to a stiffness-versus-position plot, which is shown in FIG. 7. For a single step from one stator pole to the next stator pole, FIG. 7 indicates that there is a stable equilibrium and an unstable equilibrium. For the 2RP-4SP curve, for example, the rotor and stator poles are aligned at 0 degrees (see also FIG. 2A). At this point there is zero cogging torque, and maximum positive stiffness, so in the unloaded position the CTA will come to rest at this spot. Of course, if loaded, the CTA would come to rest at the point where the cogging torque matches the load torque. Halfway between the two stator poles, at −45 and 45 degrees (see FIG. 2C), again there is no cogging torque, but the opposite stiffness creates an unstable equilibrium point. About the aligned (0 degrees) position, the passive stiffness can be modeled by a nonlinear softening spring. This spring provides a beneficial passive series-elastic effect that is designable. During operation, stator currents can be employed to dynamically alter the spring stiffness, albeit with a power cost. However, in certain situations, this may be worthwhile.

There exist some basic relationships between CTA design parameters, maximum cogging torque (i.e., passive holding torque), and actuator compliance. Each of these can be modulated dynamically by controlling the current(s) supplied to the stator coils. Of course, other parameters, such as rotor-to-stator radius ratio and geometric stator parameters can also affect cogging torque and stiffness.

When designing a particular CTA for a particular application, the performance parameters are the torque function $\tau(\theta, I)$, where $\theta$ is the rotor angular position and I is the array of stator control currents, the step resolution ($\theta_r$), and the minimum energy required per step ($U_{step}$). The torque function is a combination of the cogging torque and the electromagnetic torque generated through stator coil currents. Other important parameters are derived from the torque function: the stiffness function ($k_\theta(\theta, I)$), and the holding torque ($\tau_h(I)$). The "passive holding torque" is the holding torque with stator coil currents equal to zero. The step resolution is determined by the number of stator poles and the gear ratio (if a transmission is included). The minimum energy per step is primarily determined by the stiffness function. There is an unstable equilibrium point when the permanent magnet rotor is midway between two stator poles. To move from one stator pole to the next, the permanent magnet rotor must overcome this energy barrier, the magnitude of which is determined by the stiffness function. The minimum energy per step is the magnitude of this energy barrier plus the friction energy that must be overcome. These performance parameters are determined by the design parameters and system constraints. The design parameters can include the number or rotor poles ($N_r$), the number of stator poles ($N_s$), the total CTA diameter (D), the rotor diameter ($D_r$), the ratio of the coil volume to the stator-pole-material volume ($V_{rat}$), and the gear ratio (r). Some of these parameters are shown in FIG. 2C.

Other design variables are taken into consideration when designing a particular CTA to increase or maximize cogging torque, such as the gap G (see FIG. 1A) between outer curvilinear surfaces 130 of the permanent rotor magnets 106 and inner curvilinear surfaces 132 of each of the stator poles 112a-d. Other design variables include the geometry of each stator pole 112a-d, including shoe size, width, height, thickness, material, etc. Regarding the geometry of each stator pole for a particular design, the angle between equilibrium points is particularly relevant in designing the stator poles (see e.g., the 90 degree angle between stator pole 112a and 112b). Such angle can be less than the 90 degree example (see e.g., FIGS. 13A and 14A, each having an angle less than 90 degrees between adjacent stator poles).

Additional design variables such as system constraints include total size and mass of a particular CTA (e.g., CTA length for a given CTA diameter), maximum allowable current and voltage from an amplifier, and maximum operating heat generation. Note that magnetic saturation in the stator material can occur, and may affect the resulting torque curve.

As described above, the minimum energy required per step will be determined by the specific CTA design. Generally, a motion to effectuate a step will consume more energy than the minimum energy possible for a particular CTA. In some examples, to improve energy efficiency, operations for regeneration of energy may be incorporated into a particular CTA, as also mentioned above. For instance, as the permanent magnet rotor approaches a stator pole where it will rest or stop, the stator pole coils could be switched over to a regeneration circuit (see e.g., FIG. 9A) that would either charge the battery or a temporary storage capacitor.

The following example illustrates that the passive behavior of a particular CTA for a given application can be designed given the parameterized model. Any particular CTA will have a certain minimum step resolution ($\theta_r$), which depends on the number of rotor and stator poles ($N_r$ and $N_s$). The tradeoff between step resolution and passive holding torque ($\tau_h$ (I=0)) can be mediated by virtue of a gear ratio (r) and total CTA diameter (D). That is, a larger CTA would yield larger holding torque for the same resolution. It is desirable to independently specify the passive holding torque ($\tau_{out}$ (I=0), and stiffness ($k_{out}(\theta_{out}, I=0)$ at the output of any gearing and the step resolution ($\theta_r$) by means of selecting the design parameters. However, these output variables are interdependent such that only two can be independently selected. Thus, a particular CTA will be defined by the following relationships, which illustrate the possible design space and a potential design process:

$$\theta_r = \frac{2\pi}{N_r r}[NP \qquad 4)$$

$$\tau_{out}(I=0) = [\tau_h(I=0)r \qquad 5)$$
$$\text{where}$$
$$\tau_h(I=0) = f(D, D_r, V_{rat}, N_r, N_p)$$

$$k_{out}(\theta_{out}, I=0) = k(\theta, I=0)r \qquad 6)$$
$$\text{where}$$
$$k(\theta, I=0) = g(D, D_r, V_{rat}, N_r, N_p)$$

where $\theta$ is the angular displacement of the CTA, $\theta_{out}$ is the angular displacement at the output of the gear (i.e., $\theta_{out} = \theta/r$), and f and g are invertible parameterized functions that can be determined through modeling.

The following algorithm is one example of how to design a particular CTA:
1. Specify the number of rotor and stator poles ($N_r$ and $N_s$) and the gear ratio (r) to select the desired resolution according to equation (4).
2. Specify the total CTA diameter (D) such that volume and size constraints are not violated. Adjust parameters $D_r$ and $V_{rat}$ until the desired passive holding torque ($\tau_{out}$(I=0)) is achieved.
3. The passive stiffness function $k(\theta_{out}, I=0)$ is now totally defined. If a different stiffness function is desired in operation, it can be actively controlled with variations in applied current.

Similar algorithms contemplated herein can start with other design variables and specify the desired holding torque and stiffness function. However, in all or most cases, one performance variable will not be independently selectable. Other variables can also determine the minimum energy per step, such as the following performance parameters: Torque function ($\tau(\theta, I)$) (including holding torque ($\tau_h(I)$) and stiffness ($k(\theta, I)$)); step resolution ($\theta_r$); and minimum energy per step ($U_{step}$). Other variables include the following design parameters: number of rotor poles ($N_r$); number of stator poles ($N_s$); total CTA diameter (D); CTA rotor diameter ($D_r$); coil to stator volume ratio ($V_{rat}$); and gear ratio (r).

In one experiment to test or validate a particular CTA with quasi-static and dynamic models, a benchtop test could be set up using the "human ankle" CTA example mentioned above. FIG. 9A shows an example of such a benchtop test setup. The test involves creating experimental torque curves by establishing a set of static stator-coil currents and a static externally applied torque, and recording the equilibrium angle of the rotor. An external load can be applied from a direct-drive torque controlled motor coupled to the CTA by means of a double capstan drive (similar to the kinematics of the commercial Geomagic Phantom Premium haptic device). Using a large rotational plate provides a very low friction and inertia, but can contain mounting holes to attach inertial loads so that both externally applied and inertial loads can be evaluated independently. Note that the system can be oriented horizontally so that gravitational loads will not affect results. Torque and position sensing capability of the CTA can also be validated. Additionally, the setup enables energy-regeneration operations by switching the amplifier on one of the stator poles and connecting it to a regeneration circuit, and the direct-drive motor could be removable for the energy-regeneration experiments.

Loads and inertias typical of those experienced by a human ankle can be applied, and the performance of the CTA can be evaluated against the desired specifications. Finally, the system can be driven with state-of-the art motor selected to meet the human-ankle specifications and a comparison of energy consumption for various tasks can be made.

The same benchtop test setup can also be used for performing or testing each of the motion-primitive tasks described above. In such testing, dynamic stator-current trajectories can be applied, and the direct-drive motor can serve as an external (disturbance) load that is independent of inertia, which enables simulation of moving inertial loads both in and against the direction of the externally applied load.

Figure 13A:
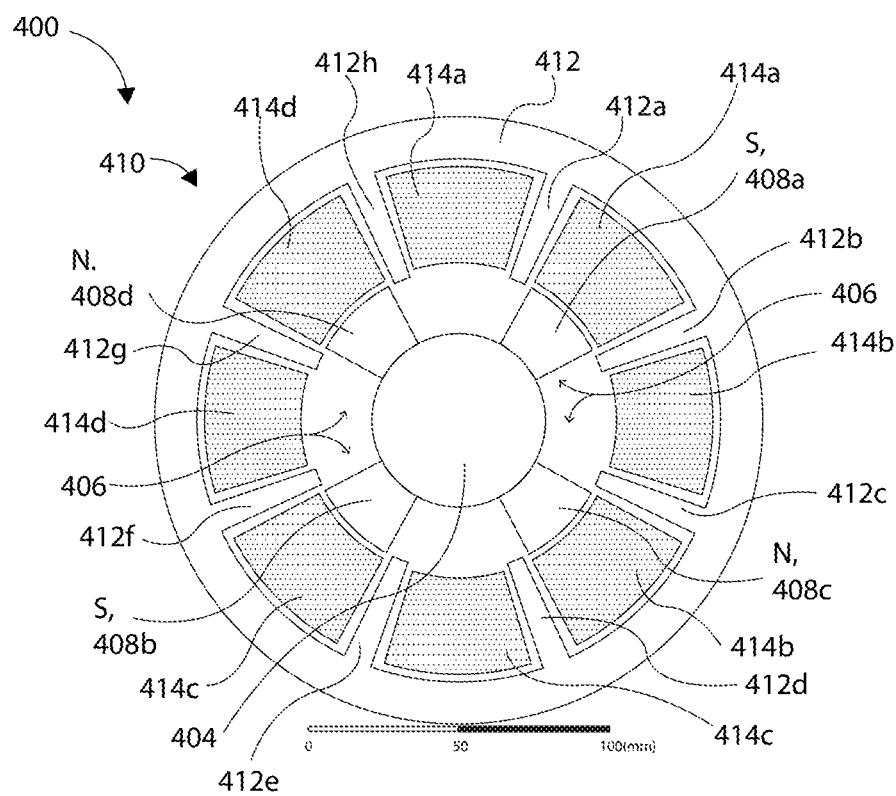
FIG. 13A is a 2D schematic of a CTA having 4 rotor poles and 8 stator poles at a stable position of minimum (zero) cogging torque in accordance with an example of the present disclosure.
Figure 13B:
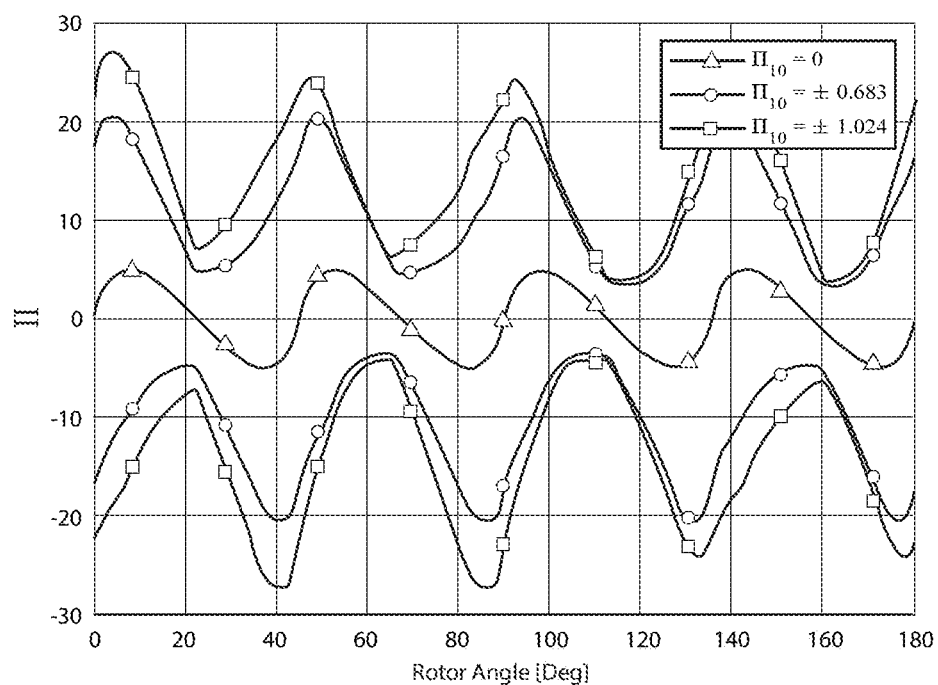
FIG. 13B is a graph of performance data associated with the CTA of FIG. 13A.

FIG. 13A illustrates a CTA 400 in accordance with an example of the present disclosure, and FIG. 13B is graph that plots performance data associated with the CTA 400. Note that the CTA 400 can have the same or similar design parameters, benefits, and operations as exemplified above regarding the CTA 100, and other examples discussed herein. Further note that the CTA 400 can be incorporated with a joint module, such as described regarding FIG. 1B and elsewhere herein. Accordingly, the CTA 400 can comprise an output shaft 404 rotatable about and defining an axis of rotation, and a permanent magnet rotor 406 comprising a pair of north magnetic poles 408*a* and 408*b* attached to the output shaft 404, and a pair of south magnetic poles 408*c* and 408*d* attached to the output shaft 404. Note that the magnetic poles 408*a-d* are equally spaced apart from each other in an alternating manner and around an outer circumferential surface of the output shaft 404 (i.e., a space or gap exists radially between adjacent rotor poles). The combination of the magnetic poles 408*a-d* and the output shaft 404 may be termed "a rotor" as termed herein. A stator device 410 can surround the permanent magnet rotor 406, and can comprise a ferromagnetic pole body 412 that includes a plurality of ferromagnetic stator poles 412*a-h* each wrapped in a conductive wire 414*a-d*, such as a copper wire forming a stator coil. A stator member or support structure can be attached to the ferromagnetic pole body 412, and can act as an input member (such as a robotic support member), so that the support structure and the ferromagnetic pole body 412 rotate together about the axis of rotation relative to the permanent magnet rotor 406. Notably, the ferromagnetic stator poles 412*a-h* are sized and spaced apart radially from each other, and spaced from the permanent magnet rotor 406, to increase or maximize the cogging torque. The space between adjacent stator poles 412*a-h* (where the copper coils are situated) can be known as the "slot" between stator poles.

EXAMPLE

Figure 14A:
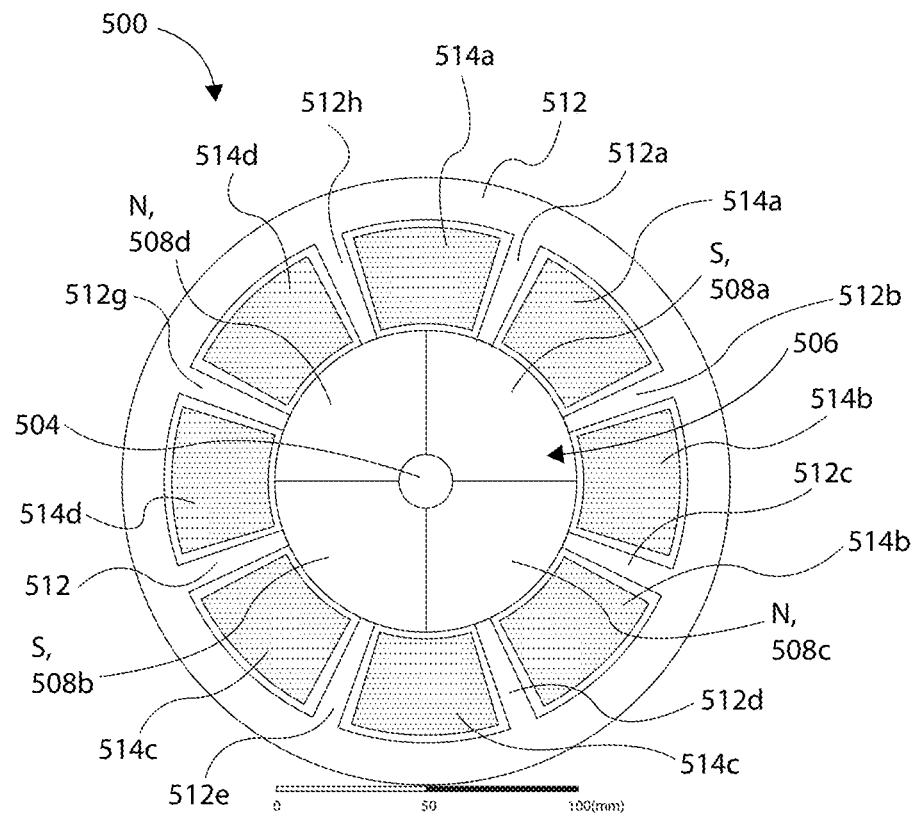
FIG. 14A is a 2D schematic of a CTA at a stable position of minimum (zero) cogging torque in accordance with an example of the present disclosure.
Figure 14B:
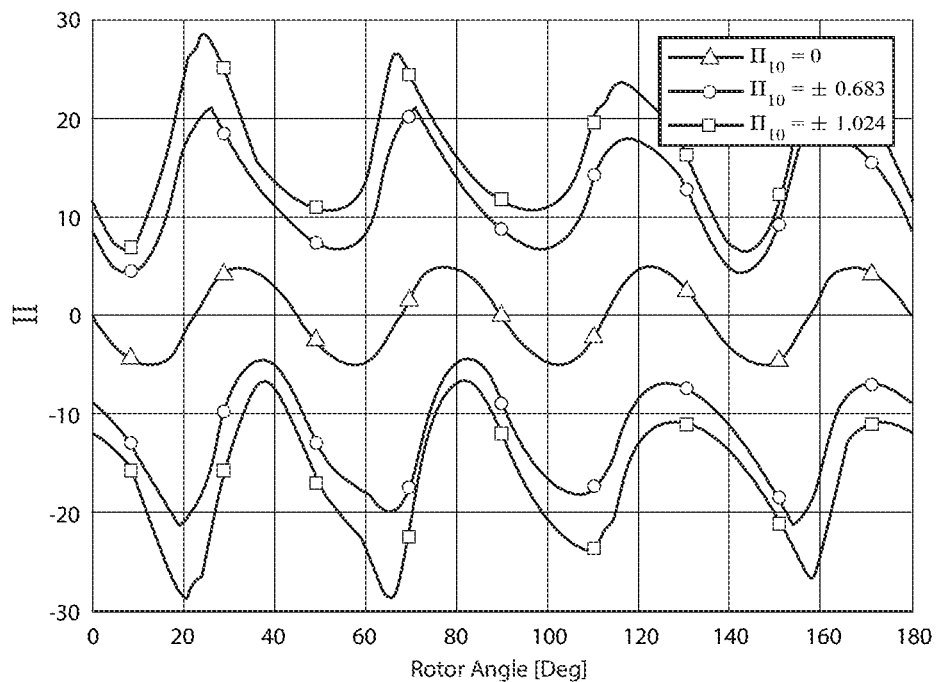
FIG. 14B is a graph of performance data associated with the CTA of FIG. 14A.

FIG. 14A illustrates a CTA 500 in accordance with an example of the present disclosure, and FIG. 14B is a graph that plots performance data associated with the CTA 500. Note that the CTA 500 can have the same or similar design parameters, benefits, and operations as exemplified above regarding the CTA 100, and other examples discussed herein. Further note that the CTA 500 can be incorporated with a joint module, such as described regarding FIG. 1B and elsewhere herein. Accordingly, the CTA 500 can comprise an output shaft 504 rotatable about and defining an axis of rotation, and a permanent magnet rotor 506 comprising a pair of north magnetic poles 508*a* and 508*b* attached to the output shaft 504, and a pair of south magnetic poles 508*c* and 508*d* attached to the output shaft 504. Note that the magnetic poles 508*a-d* are biased or interfaced to each other in an alternating manner and around an outer circumferential surface of the output shaft 504. A stator device 510 can surround the permanent magnet rotor 506, and can comprise a ferromagnetic pole body 512 that includes a plurality of ferromagnetic stator poles 512*a-h* each wrapped in a conductive wire 514*a-d*, such as a copper wire forming a stator coil. A stator member or support structure can be attached to the ferromagnetic pole body 512, and can act as an input member (such as a robotic support member), so that the support structure and the ferromagnetic pole body 512 rotate together about the axis of rotation relative to the permanent magnet rotor 506.

With regard to the CTAs 400 and 500, both may have a small "embrace" (i.e., fraction of stator arc that is tooth, as opposed to slot). The CTA 400 may have a relatively small "fractional arc angle" (i.e., fraction of rotor angle that has permanent magnet), and the CTA 500 may have a fractional arc angle close or near to 1.

In characterizing the torque that the CTAs 400 and 500 can produce (and other CTAs contemplated herein), 13 different properties are considered, as indicated in Table (1) provided below. Assuming current density is J=0, then the "total torque" simplifies to the "cogging torque" (i.e., the torque experienced when the motor is turned off).

TABLE 1

| Variable | Symbol | Dimension |
| --- | --- | --- |
| Total Torque | $T_{tot}$ | N·m |
| Rotor Radius | $R_r$ | m |
| Magnet Thickness | $R_m$ | m |
| Air-gap | $R_g$ | m |
| Slot Depth | $R_s$ | m |
| Yoke Thickness | $R_y$ | m |
| Length | L | m |
| Steel Permeability | $\mu_y$ | $\dfrac{N \cdot s^2}{C^2}$ |
| Steel Magnetic Saturation | $B_y$ | $\dfrac{N \cdot s}{C \cdot m}$ |
| Magnetic Permeability | $\mu_m$ | $\dfrac{N \cdot s^2}{C^2}$ |

TABLE 1-continued

| Variable | Symbol | Dimension |
| --- | --- | --- |
| Magnetic Coercivity | $H_{cm}$ | $\frac{C}{s \cdot m}$ |
| Embrace | E | 1 |
| Fractional Arc Angle | F | 1 |
| Current Density | J | $\frac{C}{s \cdot m^2}$ |

The Buckingham Pi theorem can be implemented to perform dimensional analysis on the design of the CTAs 400 and 500 (and other CTAs contemplated herein) to determine possible independent variables that affect design. Three parameters (rotor-magnet permeability, rotor-magnet coercivity, and the rotor radius) can be used to nondimensionalize all other parameters. The nondimensional total torque (Pi) can be characterized by 10 independent nondimensional parameters, namely $Pi_1$ through $Pi_{10}$, as indicated in Variable List below.

Variable List (1)

$$a = f(a_1, \ldots, a_3, b_1, \ldots, b_{10})$$

$$T_{tot} = f(H_{cm}[?] \mu_m[?] R_r[?] E[?] F[?] R_m[?] R_g[?] R_s[?] R_y[?] L[?] \mu_y[?] B_y[?] J[?])$$

$$PI = \frac{T_{tot}}{\mu_m * H_{cm}^2 * R_r^3}$$

$$PI_1 = E$$

$$PI_2 = F$$

$$PI_3 = \frac{R_m}{R_r}$$

$$PI_4 = \frac{R_g}{R_r}$$

$$PI_5 = \frac{R_s}{R_r}$$

$$PI_6 = \frac{R_y}{R_r}$$

$$PI_7 = \frac{L}{R_r}$$

$$PI_8 = \frac{\mu_y}{\mu_m}$$

$$PI_9 = \frac{B_y}{\mu_m * H_{cm}}$$

$$PI_{10} = \frac{J * R_r}{H_{cm}}$$

Note that cogging torque can be characterized by the first nine variables (i.e., $Pi_1$ through $Pi_9$). For wide range of motor lengths, the length ($Pi_7$) is nearly exactly linearly related to PI (i.e., double the length while holding all other parameters constant will result in double torque). The gap between the rotor and the stator ($Pi_4$) can be designed as small as possible, which will be ultimately dictated by manufacturing tolerances, in order to maximize cogging torque.

A Monte Carlo simulation of 400 different CTAs designs was performed, in which parameters were randomly selected from reasonable ranges of values. For each design, the maximum cogging torque was calculated over the full cycle of rotor motion in 2 degree increments. For the best-performing designs of the Monte Carlo simulation, a gradient-ascent optimization was performed to further improve the maximum cogging torque. The two designs that resulted in the best performance are shown Table 2 below, as corresponding to CTA 400 and CTA 500, respectively.

TABLE (2)

| PI Terms | Design A (FIG. 13A) | Design B (FIG. 14A) |
| --- | --- | --- |
| PI | 4.95 | 4.97 |
| $PI_1$ | 0.142 | 0.10 |
| $PI_2$ | 0.405 | 0.99 |
| $PI_3$ | 0.422 | 0.772 |
| $PI_4$ | 0.01 | 0.01 |
| $PI_5$ | 0.737 | 0.692 |
| $PI_6$ | 0.298 | 0.316 |
| $PI_7$ | 20 | 20 |
| $PI_8$ | 4545.4 | 4545.4 |
| $PI_9$ | −3.456 | −3.456 |

Note that both CTAs 400 and 500 resulted in Pi=5.0. Because it is known that $Pi_7$ enters approximately linearly and it was fixed at $Pi_7$=20, a new output variable Pi/$Pi_7$ can be performed, which resulted in optimal Pi/$Pi_7$=0.25 (approximately). The value of $Pi_4$ was fixed at $Pi_4$=0.01. For $Pi_8$ and $Pi_9$, values from high-performance steels were used, such as steels used in fabrication of motors.

With reference to the graphs of FIGS. 13B and 14B, these graphs plot total torque (i.e., maximum cogging torque+ electromagnetic torque) for each of the designs of FIGS. 13A and 14A, respectively. The middlemost line, indicated by the "triangular" designation in the legend, is generated from J=0 A/mm² (cogging torque), and $H_{cm}$=−292989.7 A/m, and $R_r$=0.05 m. The upper and lower most lines, indicated by the "square" designation in the legend, are generated from J=±6 A/mm², and $H_{cm}$=−292989.7 A/m, and $R_r$=0.05 m. Finally, middle lines indicated by the "circle" designation in the legend are generated from J=±4 A/mm², and $H_{cm}$=−292989.7 A/m, and $R_r$=0.05 m.

Note that the CTAs 400 and 500 are merely examples of possible configurations, and it should be appreciated that any number of suitable designs could be generated for particular size and performance of a particular CTA for a particular application, where cogging torque is optimized or maximized.

The CTAs contemplated herein can be used or operated as a radial-flux actuator, motor, or machine, such as described and shown in FIGS. 1A, 2A-2C, 13A and 14A. Alternatively, any of the CTAs described herein can be made as an axial-flux actuator, motor, or machine (not shown), with slight modifications that would be readily known to those skilled in the art.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. An electromagnetic actuator for non-continuous rotation, comprising:
   a support structure;
   an output shaft rotatable about and defining an axis of rotation;

a permanent magnet rotor comprising at least two magnetic poles attached to the output shaft; and a stator device comprising a ferromagnetic pole body attached to the support structure and surrounding the at least two magnetic poles, the ferromagnetic pole body having at least four ferromagnetic stator poles each wrapped in a conductive wire to define a stator coil, wherein the at least four ferromagnetic stator poles are sized, and spaced radially from each other so as to define a maximum cogging torque of the electromagnetic actuator, wherein a total torque of the electromagnetic actuator is within a same order of magnitude as the maximum cogging torque, wherein the same order of magnitude is less than ten times.

2. The electromagnetic actuator of claim 1, further comprising a controller operably coupled to the stator coils for controlling an electrical field applied to one or more of the stator coils, wherein the controller is operable to implement one or more motion primitives associated with rotational movement of the output shaft.

3. The electromagnetic actuator of claim 2, wherein the one or more motion primitives comprises control over mechanical impedance, such that the controller is operable to modify a magnetic spring or damping value of the electromagnetic actuator by supplying an electrical field to at least one of the stator coils.

4. The electromagnetic actuator of claim 2, wherein the one or more motion primitives comprise control over point-to-point sub-movements of the permanent magnet rotor in a rotational step movement relative to the stator device, the electromagnetic actuator further comprising a force sensor associated with the output shaft to determine a torque load applied to the output shaft, wherein the controller operates to apply an electrical field to opposing stator coils to rotate the permanent magnet rotor from a first step position to a second step position based on a sensed torque load on the output shaft, wherein, when in the second rest step position, the controller operates to remove the electrical field, such that one of the stator poles magnetically maintains the position of the permanent magnet rotor in the second rest step position.

5. The electromagnetic actuator of claim 4, wherein the controller is operable to cause rotation of the output shaft and the permanent magnet rotor in a plurality of consecutive 10 step positions over a given period of time by controlling application of an electrical field to and from any of the stator coils.

6. The electromagnetic actuator of claim 2, further comprising a position sensor and a force sensor each operably coupled to the controller for determining a torque load applied to the output shaft and for determining an angular position of the permanent magnet rotor.

7. The electromagnetic actuator of claim 1, further comprising a transmission coupled to the output shaft for decreasing an amount of angular rotation of the output shaft during step movement of the permanent magnet rotor between adjacent stator poles.

8. The electromagnetic actuator of claim 1, wherein the at least four stator poles comprises four to twelve stator poles.

9. The electromagnetic actuator of claim 1, wherein the total torque comprises a combination of the maximum cogging torque and an applied electromagnetic torque, wherein the applied electromagnetic torque is greater than the maximum cogging torque, such that the applied electromagnetic torque is sufficient to move overcome the maximum cogging torque to move the permanent magnet rotor from one step position to an adjacent step position relative to the stator device.

10. The electromagnetic actuator of claim 1, wherein the electromagnetic actuator is operable to support a torque load applied to the output shaft, whereby a magnetic force between the permanent magnet rotor and the stator poles is sufficient to hold the permanent rotor magnet and the output shaft in a holding position without supplying an electrical field to any of the stator coils.

11. The electromagnetic actuator of claim 1, wherein the total torque is less than 5 times the maximum cogging torque.

12. The electromagnetic actuator of claim 1, wherein the total torque is less than 1 times the maximum cogging torque.

13. The electromagnetic actuator of claim 1, wherein the maximum cogging torque is further defined by one or more variables selected from the group consisting of number of rotor poles, number of stator poles, gear ratio, actuator diameter, torque function, step resolution, minimum energy per step, rotor diameter, coil to stator volume ratio, and combinations thereof.

14. A robotic system comprising at least one robotic joint incorporating the electromagnetic actuator of claim 1 for operating the at least one robotic joint.

15. An exoskeleton comprising at least one joint module associated with a human joint, the at least one joint module comprising the electromagnetic actuator of claim 1 for operating the at least one joint module.

16. A prosthesis comprising at least one prosthetic joint incorporating the electromagnetic actuator of claim 1 for operating the at least one prosthetic joint.

17. A method of operating the electromagnetic actuator of claim 1, the method comprising applying a torque load to the output shaft and applying an electrical field to opposing stator coils to rotate the output shaft from a first position to a second position sufficient to overcome the torque load, and then removing the electrical field from the opposing stator coils, such that the output shaft remains in the second position to support the torque load by virtue of a magnetic force generated by the permanent magnet rotors and the ferromagnetic pole body.

18. A system for controlling rotational movement of a joint, comprising:

first and second support members rotatably coupled to each other and that define a joint rotatable about an axis of rotation;

an electromagnetic joint module comprising an input member coupled to the first support member, and an output shaft coupled to the second support member, such that the input member and the output shaft are rotatable about the axis of rotation, the electromagnetic joint module comprising at least two magnetic poles attached to the output shaft, and a ferromagnetic pole body attached to the input member and comprising a plurality of ferromagnetic stator poles each wrapped in a conductive wire to define a stator coil, wherein at least two magnetic poles and the plurality of ferromagnetic stator poles are configured to define a maximum cogging torque, wherein a total torque of the electromagnetic joint module is within a same order of magnitude as the maximum cogging torque, wherein the same order of magnitude is less than ten times; and a controller operably coupled to each stator coil for controlling non-continuous rotational movement of the joint.

19. The system of claim 18, wherein the controller is operable to control non-continuous rotation of the joint in less than 90 degrees of rotation in a single step operation in response to applying an electrical field to opposing stator coils and removing the electrical field from the opposing stator coils.

20. The system of claim 18, wherein the controller is operable to control non-continuous rotation of the joint in less than 90 degrees of rotation in a single step operation in response to applying an electrical field to opposing stator coils and removing the electrical field from the opposing stator coils.

21. The system of claim 18, wherein the wherein the total torque is less than 5 times the maximum cogging torque.

* * * * *